United States Patent
Hayes et al.

(10) Patent No.: US 10,244,977 B2
(45) Date of Patent: Apr. 2, 2019

(54) SYSTEM AND METHOD FOR EARLY DETECTION OF MILD TRAUMATIC BRAIN INJURY

(71) Applicant: University of Maine System Board of Trustees, Bangor, ME (US)

(72) Inventors: Marie J. Hayes, Hampden, ME (US); Ali Abedi, Orono, ME (US)

(73) Assignee: University of Maine System Board of Trustees, Bangor, ME (US)

( * ) Notice: Subject to any disclaimer, the term of this patent is extended or adjusted under 35 U.S.C. 154(b) by 693 days.

(21) Appl. No.: 14/948,667

(22) Filed: Nov. 23, 2015

(65) Prior Publication Data

US 2016/0183861 A1    Jun. 30, 2016

Related U.S. Application Data

(63) Continuation of application No. 13/106,451, filed on May 12, 2011, now Pat. No. 9,192,333.
(Continued)

(51) Int. Cl.
*A61B 5/00* (2006.01)
*A61B 5/02* (2006.01)
(Continued)

(52) U.S. Cl.
CPC ........ *A61B 5/4064* (2013.01); *A61B 5/02055* (2013.01); *A61B 5/11* (2013.01); *A61B 5/1114* (2013.01); *A61B 5/4815* (2013.01); *A61B 5/6892* (2013.01); *A61B 5/7203* (2013.01); *A61B 5/7257* (2013.01); *A61B 5/7264* (2013.01); *A61B 5/002* (2013.01); *A61B 5/1118* (2013.01); *A61B 5/4812* (2013.01); *A61B 2562/028* (2013.01);
(Continued)

(58) Field of Classification Search
CPC ....... A61B 5/7264; A61B 5/11; A61B 5/4064; A61B 5/1114; A61B 5/4815; A61B 5/6892; A61B 5/02055; A61B 5/7203; A61B 5/7257; A61B 2562/0247; A61B 2562/164; A61B 5/002; A61B 2562/168; A61B 5/4812; A61B 2562/028
See application file for complete search history.

(56) References Cited

U.S. PATENT DOCUMENTS

| | | | | |
|---|---|---|---|---|
| 5,571,973 A | * | 11/1996 | Taylot | A61B 5/1036 73/862.046 |
| 5,989,700 A | | 11/1999 | Krivopal | |

(Continued)

FOREIGN PATENT DOCUMENTS

WO    WO 2009120270 A2 * 10/2009 ........... A47C 27/082

OTHER PUBLICATIONS

Verma et al., "Sleep Disorders in Chronic Traumatic Brain Injury", 2007, J. Clin. Sleep Med. vol. 3 No. 4 pp. 357-362.*
(Continued)

*Primary Examiner* — Regis J Betsch
(74) *Attorney, Agent, or Firm* — MacMillan, Sobanski & Todd, LLC

(57) ABSTRACT

A wireless system and methods for non-invasive detection of brain injury that includes a detection device for reliable monitoring and analyzing of sleep movement in comparison with normal sleep movement architecture to identify dampened sleep movement patterns indicative of brain injury.

22 Claims, 14 Drawing Sheets

Related U.S. Application Data

(60) Provisional application No. 61/428,295, filed on Dec. 30, 2010.

(51) Int. Cl.
  *A61B 5/11* (2006.01)
  *A61B 5/0205* (2006.01)

(52) U.S. Cl.
  CPC . *A61B 2562/0247* (2013.01); *A61B 2562/164* (2013.01); *A61B 2562/168* (2013.01)

(56) References Cited

U.S. PATENT DOCUMENTS

| | | |
|---|---|---|
| 6,530,884 B2 | 3/2003 | Balkin et al. |
| 6,579,233 B2 | 6/2003 | Hursh |
| 6,743,167 B2 | 6/2004 | Balkin et al. |
| 7,207,938 B2 | 4/2007 | Hursh |
| 7,306,564 B2 | 12/2007 | Nakatani et al. |
| 7,766,827 B2 | 8/2010 | Balkin et al. |
| 7,898,426 B2 | 3/2011 | Rai et al. |

OTHER PUBLICATIONS

Rauhala, "Detection of periodic leg movements with a static-chargesensitive bed", 1996, J. Sleep Res vol. 5, pp. 246-250.*
Ferri et al., "New Approaches to the Study of Periodic Leg Movements During Sleep in Restless Legs Syndrome", 2006, SLEEP, vol. 29, No. 6, pp. 759-769.*
Mahon et al., "Behaviour of spectral entropy, spectral edge frequency 90%, and alpha and beta power parameters during lowdose propofol infusion", 2008, British Journal of Anaesthesia 101 (2): 213-21.*
Alihanka, "A new method for long-term monitoring of the ballistocardiogram, heart rate, and respiration", 1981, Am. J. Physiol. 240 (Regulatory Integrative Comp. Physiol. 9): R384-R392.*
Alain Muzet, "Alteration of sleep microstructure in psychiatric disorders", 2005 Dialogues Clin Neurosci. Dec. 2005; 7(4): 315-321.*
Parrino et al., "CAP, epilepsy and motor events during sleep: the unifying role of arousal", 2006, Sleep Medicine Reviews (2006) 10, 267-285.*
Jan Magne Tjensvold, "Comparison of the IEEE 802.11, 802.15.1, 802.15.4 and 802.15.6 wireless standards", 2008, http://janmagnet.files.wordpress.com/2008/07/comparison-ieee-802-standards.pdf.*
Beetar et al., "Sleep and pain complaints in symptomatic traumatic brain injury and neurologic populations", Archives of Physical Medicine and Rehabilitation, 1996, vol. 77, No. 1.2, pp. 1298-1302.
Castriotta et al., "Sleep disorders associated with traumatic brain injury", Archives of Physical Medicine and Rehabilitation, 2001, vol. 82, No. 10, pp. 1403-1406.
Durmer et al., "Neurocognitive consequences of sleep deprivation", Seminars in Neurology, 2005, vol. 25, No. 1, pp. 117-129.
Ferri et al., "New Approaches to the Study of Periodic Leg Movements During Sleep in Restless Legs Syndrome", Sleep, 2006, vol. 29, No. 6, pp. 759-769.
Fischer, "United States military casualty statistics: operation Iragi freedom and operation enduring freedom", CRS report for Congress, Order Code RS22452, 2008.
Hayes et al., "Apneic preterms and methylxanthines: arousal deficits, sleep fragmentation and suppressed spontaneous movements", Journal of Perinatology, 2007, vol. 27, No. 12, pp. 782-789.
Hayes et al., "Functional analysis of spontaneous movements in preterm infants", Developmental Psychobiology, 1994, vol. 27, No. 5, pp. 271-287.
Hayes et al., "Methadone During Pregnancy: Sleep and Neurocognitive Performance in the Neonate", CPDD 72nd Annual Meeting, Scottsdale, Arizona, p. 68, Abstract #271.
Hayes et al., "Spontaneous motility in premature infants: features of behavioral activity and rhythmic organization", Developmental Psychobiology, 1993, vol. 26, No. 5, pp. 279-291.
Hayes, "Movement and early sleep development", Invited lecture for the Israeli Science Foundation Meeting of Motor and Sleep Development, Haifa University, Haifa, Israel, 2010.
Hibbard et al., "Undiagnosed health issues in individuals with traumatic brain injury living in the community", The Journal of Head Trauma Rehabilitation, 1998, vol. 13, No. 4, pp. 47-57.
Jansson et al., "Maternal methadone dosing schedule and maternal fetal behavior", Journal of Maternal-Fetal and Neonatal Medicine, 2009, vol. 22, No. 1, pp. 29-30.
Mahon et al., "Behaviour of spectral entropy, spectral edge frequency 90%, and alpha and beta power parameters during low-dose propofol infusion", British Journal of Anaesthesia, 2008, vol. 101, No. 2, pp. 213-221.
McNamara et al., "Spontaneous arousal activity in infants during NREM and REM sleep", The Journal of Physiology, 2002, vol. 538, No. 1, pp. 263-326.
Muzet, "Alteration of sleep microstructure in psychiatric disorders", Dialogues in Clinical Neuroscience, 2005, vol. 7, No. 4, pp. 315-312.
Ouellet et al., "Insomnia following traumatic brain injury: a review", Neurorehabil Neural Repair, 2004, vol. 18, No. 4, pp. 187-198.
Ouellet et al., "Subjective and objective measures of insomnia in the context of traumatic brain injury: a preliminary study", Sleep Med, 2006, vol. 7, No. 6, pp. 486-497.
Paquet et al., "Wake detection capacity of actigraphy during sleep", Sleep, 2007, vol. 30, No. 7, pp. 1362-1369.
Parrino et al., "CAP, epilepsy and motor events during sleepL the unifying role of arousal", Sleep Medicine Reviews, 2006, vol. 10, pp. 267-285.
Pollard et al., "Sleep dependent memory consolidation in prodromal and first episode schizophrenia", International Early Psychosis Association, Amsterdam, Netherlands, 2010, Abstract Only.
Potts et al., "Respiratory rhythm entrainment by somatic afferent stimulation", The Journal of Neuroscience, 2005, vol. 25, No. 6, pp. 1965-1978.
Rauhala, "Detection of periodic leg movements with a static-chargesensitive bed", Journal of Sleep Research, 1996, vol. 5, pp. 246-250.
Robertson, "Human cyclic motility: Fetal-Newborn continuities and newborn state differences", Developmental Psychobiology, 1987, vol. 20, No. 4, pp. 425-442.
Sadeh et al., "Activity-based sleep-wake identification: an empirical test of methodological issues", Sleep, 1994, vol. 17, No. 3, pp. 201-207.
Schmidt, "Wireless Sleep Devices for Insomnias, Parasomnias, and Other Sleep Disorders", CleveMed, presented at Neuroscience, 2008, slide presentation; http://www.clevemed.com/clevemed_pdfs/Wireless_Sleep_Devices_for_Insomnias_Parasomnias_and_Other_Sleep_Disorders.pdf.
Segalowitz et al., "Subtle symptoms associated with self reported mild head injury", Journal of Learning Disabilities, 1995, vol. 28, No. 5, pp. 309-319.
Taylor, "Adaptive Cushion Method and Apparatus for Minimizing Force Concentrations on a Human Body", 2009, WO 2006/120270.
Tjensvold, "Comparison of the IEEE 802.11, 802.15.1, and 802.15.6 wireless standards", 2007, http://janmagnet.files.wordpress.com/2008/07/comparison-ieee-802-standards.pdf.
Troese et al., "Sleep fragmentation and evidence for sleep debt in alcohol-exposed infants", Early Human Development, 2008, vol. 84, No. 9, pp. 577-585.
Van Dongen et al., "The cumulative cost of additional wakefulness: dose-response effects on neurobehavioral functions and sleep physiology from chronic sleep restriction and total sleep:deprivation", Sleep, 2003, vol. 26, No. 2, pp. 117-126.
Verma et al., "Sleep disorders in chronic traumatic brain injury", Journal of Clinical Sleep Medicine, 2007, vol. 3, No. 4, pp. 357-362.
Walker et al., "Sleep-dependent motor memory plasticity in the human brain", Neuroscience, 2005, vol. 133, No. 4, pp. 911-917.

(56) References Cited

OTHER PUBLICATIONS

Williams et al., "Polysomnographic and quantitative EEG analysis of subjects with long-term insomnia complaints associated with mild traumatic brain injury", Clinical Neurophysiology, 2008, vol. 119, pp. 429-438.

\* cited by examiner

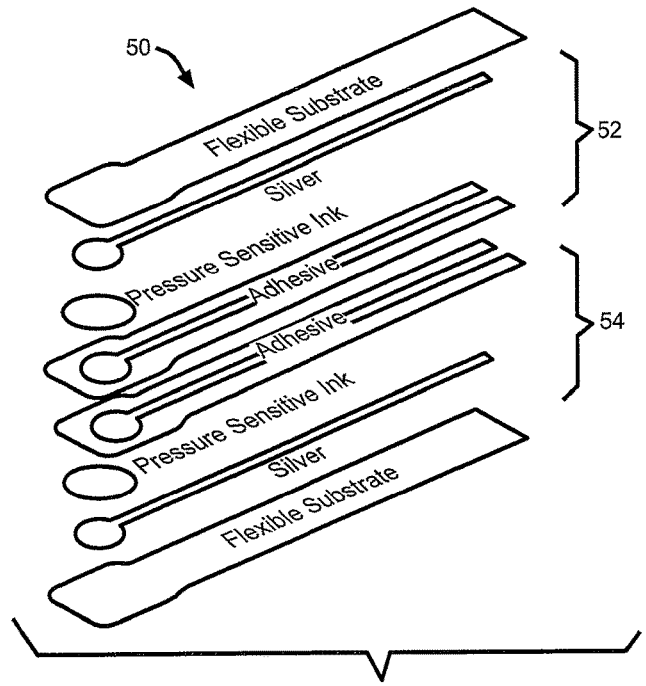
FIG. 2A
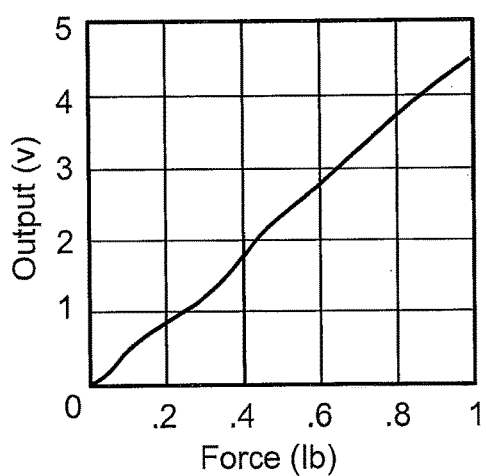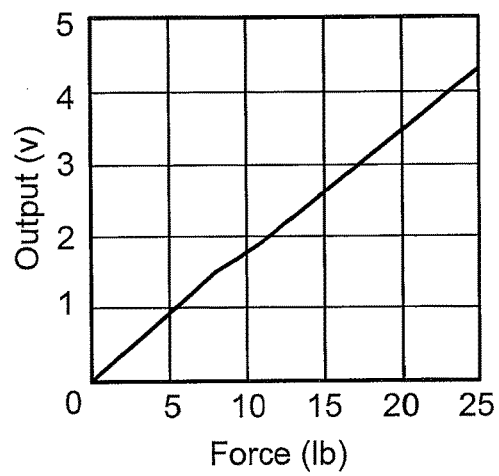
FIG. 2B

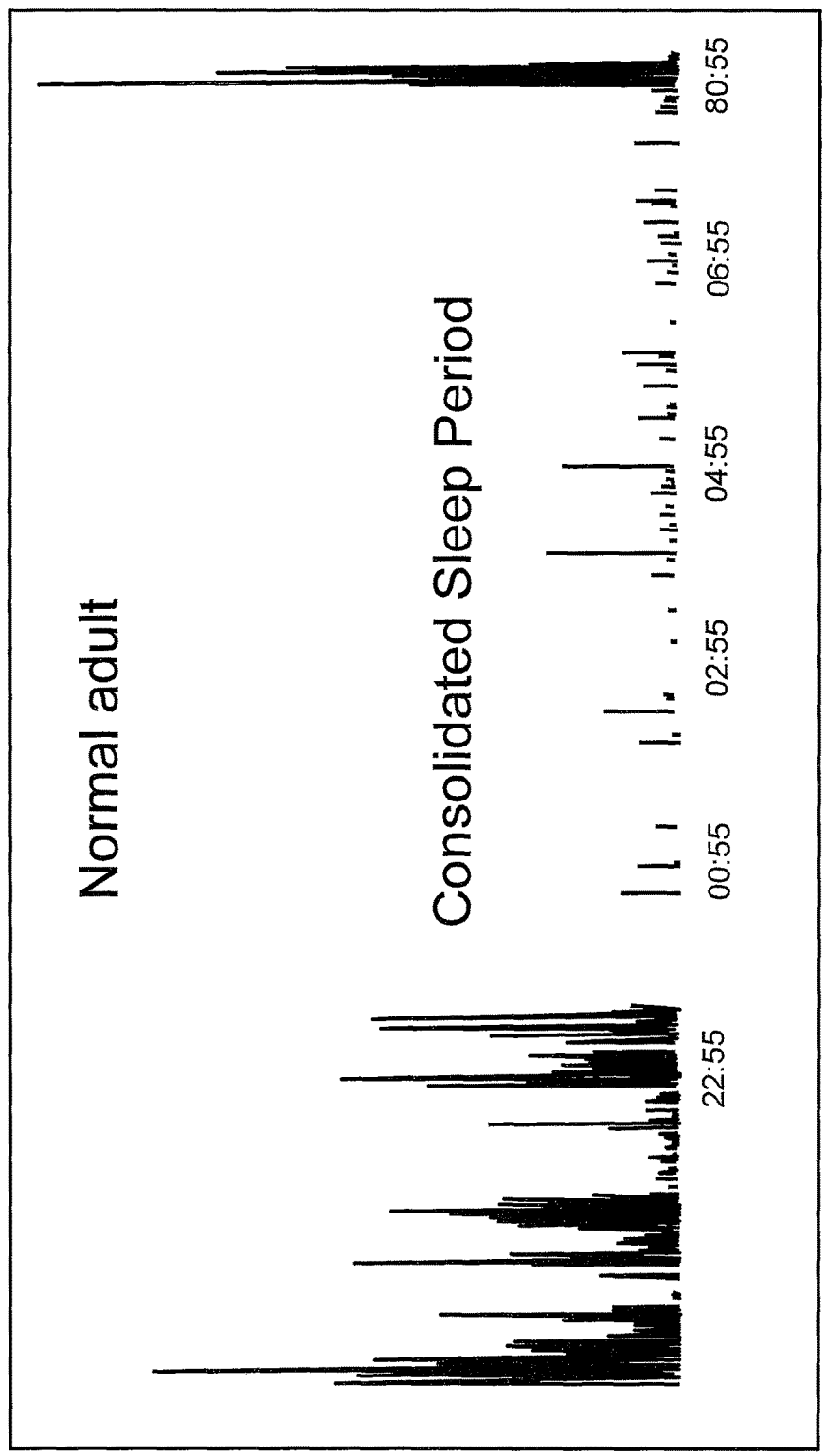

SYSTEM AND METHOD FOR EARLY DETECTION OF MILD TRAUMATIC BRAIN INJURY

CROSS-REFERENCE TO RELATED APPLICATIONS

This application is a continuation of application Ser. No. 13/106,451, filed May 12, 2011 and granted Nov. 24, 2015 as U.S. Pat. No. 9,192,333, which in turn claims the benefit of U.S. Provisional Application No. 61/428,295, filed Dec. 30, 2010, the disclosure of which is incorporated herein by reference.

FIELD OF THE INVENTION

The present invention relates to the field of medical diagnostics. More specifically, the present invention relates to identifying neurological defects in patients having one or more clinical indications or other existing symptoms of mild traumatic brain injury.

BACKGROUND OF THE INVENTION

Classic animal work in sleep science has established that adequate sleep with regard to duration and quality is required for normal cognitive performance during waking periods. In humans, "good" sleep is required for the consolidation of long term memory of the previous day's experiences. The interruption of this process by poor sleep may be an important determinant of why patients with mild Traumatic Brain Injury (mTBI) deteriorate in work and general performance over time, and may experience emotional or psychiatric consequences. Past studies have extensively quantified the striking relationships that neurocognitive performance deficits, sleep deprivation, and sleep loss have to sleep disorders associated with brain injuries.

Human studies have confirmed that quantitative measures of sleep deprivation parametrically predict cognitive performance decrements in normal and brain injured patients. The mechanistic model: A. brain injury→B. sleep disorders→C. sleep loss→D. decreased daytime alertness→E. cognitive deficits, is supported by experimental literature on sleep loss/cognitive performance decrement. As described above, it is well known that sleep disorders lead to accumulation of sleep debt correlated with diminished daytime functioning. Of particular interest is the detection of sleep disorders consequential to suspected mTBI at step B of the model, before "allostatic compensation" for accumulated sleep loss is exhausted, and alertness and cognitive functions are compromised.

In January 2008, the US Department of Defense reported a total of 5,503 soldiers currently suffering with traumatic brain injuries. Mild Traumatic Brain Injury is the most common kind of combat injury, frequently leading to cognitive deficits in attention, speed of information processing, and working long-term memory performance. As many as 30% of patients with mTBI show neurological symptoms such as, for example; headaches, dizziness, irritability, and neurocognitive deficits, long after experiencing head trauma.

Neurocognitive deficits are commonly found in patients with mTBI, as are complaints of sleep disorders, daytime sleepiness and fatigue in 70% of cases during the first six months after experiencing a concussion. It is well known that brain injury, including traumatic brain injury, is commonly accompanied by sleep disturbance and, over a short period of time, consequent sleep deprivation. As is well established, sleep deprivation leads to parametric dose-related loss of cognitive executive function, fatigue, and mood problems.

Although most cases of mTBI resolve within six to twelve months, 20-30% of patients with mTBE have persistent symptoms, most commonly headache and sleep disorders. The main symptom cluster is complaint of cognitive impairment, e.g., deficits of attention, information processing speed, working and long-term memory loss. Pharmacological, cognitive, and behavioral treatment for mTBI have had mixed success to date and mTBI has been found to be resistant to neuropsychological rehabilitation.

Early detection is critical to insure the safety of a patient with mTBI, as well as others who are dependent on the patient's functioning. Persistent cognitive fog and sleep disorders may lead to psychiatric, work, and family functional impairment. Recent studies report that cognitive confusion, memory loss, and psychiatric symptoms predict risk for a second TBI and further complicate the rehabilitative process.

While even mild brain trauma has been shown to cause neuronal damage, brain injury detection during the early post-concussive period continues to be difficult. Current screening methods with magnetic resonance imaging to establish neurological correlations of mTBI cognitive deficits have produced results that are lower than expected. The need for better screening is appreciated and new techniques are currently being developed. Axonal damage has recently been reported using diffusion tensor imaging and it is hoped that the technology may improve objective screening capabilities in the future.

Diagnosis of brain injury, particularly mTBI, or concussion as it is commonly known, is typically performed by combining imaging technology with established techniques for assessing consciousness and/or cognitive function. A conclusion of brain injury is made based on the sum of results. The Glasgow Coma Scale (GSC) is recognized as one of several reliable means for assessing the level of consciousness in subjects known to have received head injuries. The assessment tool records eye opening behavior along with verbal and motor responses to arrive at a cumulative score indicative of the level of brain injury. Patients with scores less than 14 are considered to be affected by minor brain injury. Scores of less than 13 and 9 represent moderate and severe brain injury, respectively. While GCS is a useful tool, combining brain images with only GCS scoring has proven inadequate for screening. Behavioral functioning as measured by GCS may be normal for up to a week after the injury event. Furthermore, even when early GCS scores are indicative of brain injury, too much emphasis may be placed on the complementary technologies. Accordingly, false negative screening conclusions are common despite low early GCS scores.

Thus, objective screening for mTBI is often inconclusive, particularly in the acute phase of post-trauma. Delayed diagnosis and treatment of early stage brain injury prolongs patient recovery and cognitive rehabilitation. Early detection of developing impairment is essential for intervention purposes. While monitoring changes in sleep behavior has had the potential to identify patients inflicted with brain injury that have been mischaracterized by conventional screening technology, systems and methods of screening, carefully designed to discriminate patients with traumatic brain injury from patients suffering merely from non-trauma related sleep complications, have yet been unavailable. Therefore, to overcome the shortcomings currently existing in the art, an innovative system to efficiently and reliably differentiate relatively normal sleep movement patterns from those of persons afflicted with early stage brain injuries such as mTBI following head trauma is needed.

SUMMARY OF THE INVENTION

The present invention is directed to a system and methods for detecting brain injury by obtaining and analyzing data relating to sleep movement patterns. As disclosed herein, a preferred example of the type of brain disorder to be detected by such a system and methods is early stage brain injury (mTBI) following head trauma. However, the system and methods are also provided for detecting brain injury secondary to other medical conditions such as neurotoxicity or ischemic stroke, or other neurological conditions, such as, for example, Alzheimer's or schizophrenia, associated with brain injuries which may be similarly difficult to detect using current technologies, such as, magnetic resonance imaging or computer assisted tomography.

It is an object of the present invention to provide a system for detecting early stage brain injury which is difficult to identify using conventional methods.

It is a further object of the present invention to provide a system for reliably detecting mTBI in patients following head trauma.

It is yet another object of the invention to provide improved methods for monitoring the sleep of patients suspected of having brain injury.

It is still a further objective of the invention to provide methods for processing and analyzing SM related data to improve the reliability of diagnosing brain injury such as mTBI.

The foregoing and related objects, advantages, and features of the invention should be more readily apparent to those skilled in the art after review of the following detailed description of the invention, taken together with the drawings and claims.

The present invention uniquely detects brain injury by comparing Sleep Movement (SM) normative features of sleep quality related to SM abnormalities characteristic of brain injury. To do so, the invention provides a means for monitoring and assessing the robustness of SM patterning using novel algorithms for sleep related pattern analysis. In general, sleep disorders in brain injured patients are accompanied by significant dampening of SM and the invention comprises fine-grained SM bout analysis of SM timing, frequency, duration, and vigor to yield parameters of interest that distinguish normative from putative brain injured groups.

In accordance with a first aspect of the present invention a system is disclosed for monitoring, recording, and analyzing sleep movement (SM) comprising a highly sensitive actigraphic device having a sensor array with at least one sensor and a variable sampling rate of approximately 10 Hz. The sensor may be a piezoelectric or piezoresistive based pressure sensor. Analog signals from the sensor array are digitized for signal processing, wireless transmission, and analysis. Sampling rate and data distribution are controlled by a microprocessor in accordance with stored algorithms. In a preferred embodiment of the invention, the system includes a data filtering means and data processing functions that parametrically adjust the SM data for final analysis in two stages, on board of sensor and after transmission to base station.

In a preferred exemplary embodiment of the invention, the system also includes a highly sensitive array of sensors capable of measuring SM, heart rate, and respiration with accuracy and precision required to effectively diagnose mTBI. Signals from the sensor array are conditioned by electronic circuitry before being transmitted to a nearby receiver in a wireless fashion. Signals transmitted to the receiver are processed using novel electrical engineering methods for mitigating wireless noise and interference before entering a remote base station where the data is further processed and analyzed using novel neuroscience algorithms. Alternately, a hard wire connection may be utilized to transmit data from the sensors and signal conditioning circuits to a base station the either is located near or adjacent to the sensors.

In accordance with a second aspect of the present invention, methods are disclosed for detecting brain injury in patients known have experienced trauma. Identification of brain injury is made by collecting and analyzing actigraphic data. The methods comprise steps which employ a highly sensitive actigraphic device along with novel sampling techniques and algorithms for conditioning and analyzing SM signals.

BRIEF DESCRIPTION OF THE DRAWINGS

FIG. 2A illustrates the construction of actigraphic sensors utilized in the system shown in FIG. 2.

FIG. 2B illustrates the responses of one and 25 pound sensors that are constructed as shown in FIG. 2A.

FIG. 4 illustrates the deficient sleep movement monitoring sensitivity typical of competing technology devices.

DETAILED DESCRIPTION OF THE INVENTION

Figure 1:
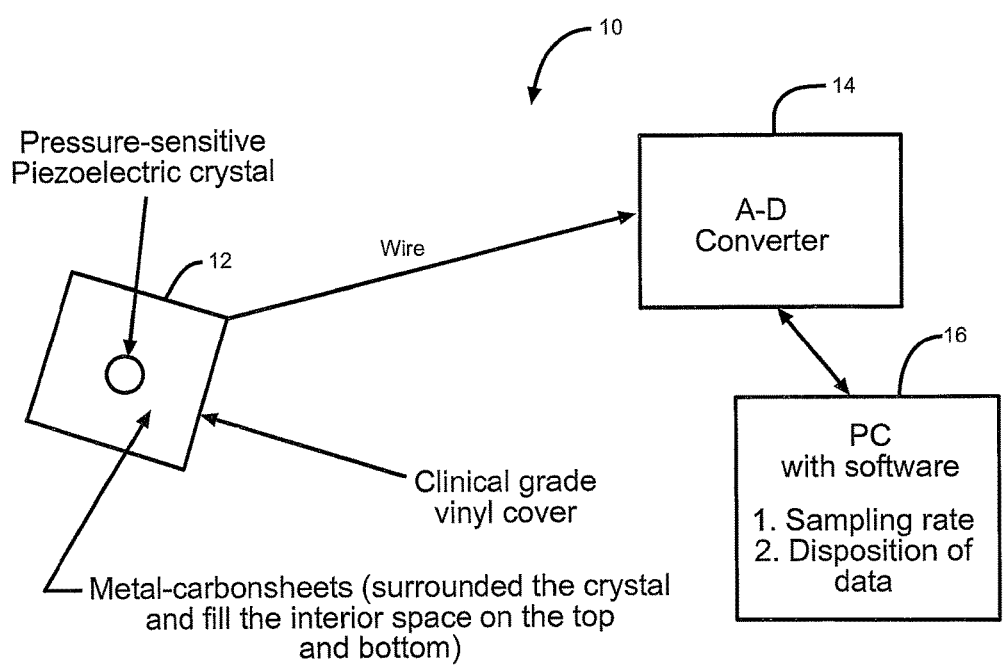
FIG. 1 is a block diagram of a simple actigraphy device.

Brain injury is associated with disturbances in brain regulation and spontaneous movements during sleep. The present invention contemplates using actigraphy as a supplement or alternative to brain injury screening with prior art imaging technologies. Timing, vigor, and duration of spontaneous movements during sleep are stable individual characteristics from fetal life to adulthood. They are distinct from full arousal events and represent a normal aspect of sleep. In humans and other vertebrates, movements during sleep occur as phasic activity during rapid eye movement sleep, as full postural changes during state change, and during brief arousals or full awakening. In animal and human models, spontaneous movements during sleep are also periodic, related to brainstem/medullary pattern generator and have characteristic and duration that is species-specific. In humans, state-independent movement periodicities have been reported for feeding in infants, rest-activity cycles in adults, and fetal movements. Brain injury is associated with disturbances in brain regulation and spontaneous movements during sleep. More particularly, the duration and timing of the sleep movements of brain injured patients deviate significantly from normal Sleep Movement (SM) patterns. In general SM in patients with brain injury is significantly dampened. The present invention detects suspected brain injury based by fine-grained temporal analysis of SM "vigor" or duration of SM bursts or bouts. Disrupted sleep microstructure is identified using parametric features and algorithms of sleep related movement bouts, e.g. criteria for SM onset and offset, using a variety of functionally relevant temporal windows. Short temporal windows relate to predictive SM microstructure and are differentiated from longer windows representative of poor sleep or sleep fragmentation related to arousal.

SM is a brainstem-generated behavior characterized by well organized, periodic bursts of movements that occur frequently throughout the sleep period. The function of SM may be to up-regulate autonomic sympathetic function during sleep and, consequently, brain oxygenation. Support for this hypothesis comes from findings from single-neuron cell recordings in the brainstem respiratory circuitry. Somatic input from movements is excitatory to Botzinger complex respiratory neurons leading to unregulated respiratory-cardiac out following movement. This mechanism is likely protective against hypoxic events during sleep.

Actigraphy, the measurement and collection of gross motor activity, can be used to record specific sleep parameters shown to correlate with self-reported poor sleep quality and fatigue. Historically, actigraphy techniques and devices have been obtrusive to natural sleep movements and postures. However, recently developed systems have been designed with sensor components that allow sleep monitored subjects to be significantly more comfortable. Such actigraphy systems may include specially designed multi-sensor bed sheets, piezoelectric mattresses, or optical sensors. Alternatively, test subjects may be fitted with commercially available limb-worn accelerometer devices. The devices are typically attached to a wrist and/or ankle by means of a strap and may include filters and data storage capabilities. Although widely available from a number of vendors, commercial accelerometer devices are typically expensive, difficult to implement, and without the sensitivity and reliability needed for serious diagnostic monitoring.

Studies have shown that as many as 70% of mTBI cases, as defined by neurological and cognitive symptoms following a concussive event, develop persistent sleep-wake disorders, e.g. hypersomnia or insomnia, daytime complaints of sleepiness and excessive fatigue. Evaluation of sleep quality can be measured through self report of daytime sleepiness, e.g., Epworth Sleepiness Scale or the Karolinska Daytime Sleepiness Scale, or objective tests of sleep deprivation such as the Mean Sleep Latency Test (MSLT). Sleep difficulty is a common complaint of both Traumatic Brain Injury (TBI) and mild Traumatic Brain Injury (mTBI) patients. When self report questionnaires and two nights of polysomnography (PSG) were compared, patients with severe TBI had more sleep disturbances than matched healthy "good sleepers". The inventors found that PSG in 10 out of 14 patients showed sleep fragmentation characterized by frequent arousals and poor sleep continuity. In hospitalized patients with recent-onset TBI and in discharged patients with a median of 29.5 months post-TBI, sleep disorders were the most common complaint along with poor daytime performance. Daytime fatigue and subjective sleepiness are demonstrated consequences of poor sleep quality and predict the depth and extent of cognitive performance loss in normal and brain injured patients. Patients with mTB have been found to have significantly worse mean sleep latency values indicative of sleep deprivation, reduced REM sleep and more light sleep indicative of a premature aging pattern. In an animal model of TBI, abnormal apoptosis in the hippocampus, a brain structure critical for memory, also have been found.

To overcome the shortcomings currently existing in the art, the present invention contemplates an innovative actigraphy system making use of algorithms related to SM and sleep disorder and that is capable of adequately monitoring without obstructing natural movement and posture. Moreover, the present invention further contemplates a SM system and methods efficiently and reliably differentiate relatively normal sleep movement patterns from those of persons afflicted with early stage brain injuries such as mTBI following head trauma In an exemplary aspect of the present invention, a system for detecting brain injury comprises an actigraphy device coupled with a means for multi-parameter algorithmic analysis is described below. Preliminary data for developing preferred sampling rates and other analysis parameters are generated using one or more simple sensors embedded in a mattress. The sensor is powered by a battery or other DC power source and is wired to an oscilloscope for detection of changes to the sensor's output.

FIG. 1 is a block diagram representing a simple brain injury detection system 10 that utilizes actigraphy. The device has at least one motion sensor 12 in close communication with the sleeping surface of a mattress. The sensor 12 is electrically connected with an analog to digital signal converter 14 and, by way of the converter, the sensor is in further communication with a computer 16 having software capable of adjusting the sensor's sampling rate and controlling the disposition of data. While a computer is shown in FIG. 1, it will be appreciated that the invention also may be practiced with a microcontroller or an Applied Specific Integrated Circuit (ASIC) that is utilized in place of the computer 16. Sleep movement of a patient suspected of brain injury is captured by the sensor 12 and provides a signal which is prepared for data analysis by the computer 16. The computer 16 includes software and algorithms based on data previously collected from populations known to be afflicted by brain injury. The software and related algorithms function to select the timing and duration of data sets to be further processed and analyzed.

Sensor arrays in actigraphic systems for measuring SM must be well placed and sensitive enough to detect minimal movement intensities. A simple but sensitive SM sensor may be fabricated by enclosing a piezoelectric based passive pressure sensor in metal-carbon sheets and covering the component with a clinical grade vinyl, leaving only a wire terminal portion to be exposed. Preferably, sensors used in brain injury detection systems are designed to provide signals at frequency ranges of approximately 0.03-10 Hz.

In preferred embodiments of the invention, the motion sensors 12 are placed in close proximity to the patient being monitored for SM such that slight movements are recorded, yet the sensor is not positioned in a way that is disruptive to the patient's sleep. Preferably, sensors are attached in close communication with the system's sleeping surface, in a location and manner which is imperceptible to the sleeping patient. In addition, or as an alternative to pressure sensors, systems for detecting brain injury may comprise actigraphic device sensors which are accelerometers (not shown). The accelerometers may be attached to the patient's limbs or other anatomy expected to be repositioned during sleep, or the accelerometer sensors may be attached to the sleeping surface in a manner similar to the placement of pressure sensors. According to a preferred embodiment of the invention, the system comprises a device having optical sensors (not shown) that are not perceived by the patient.

Figure 2:
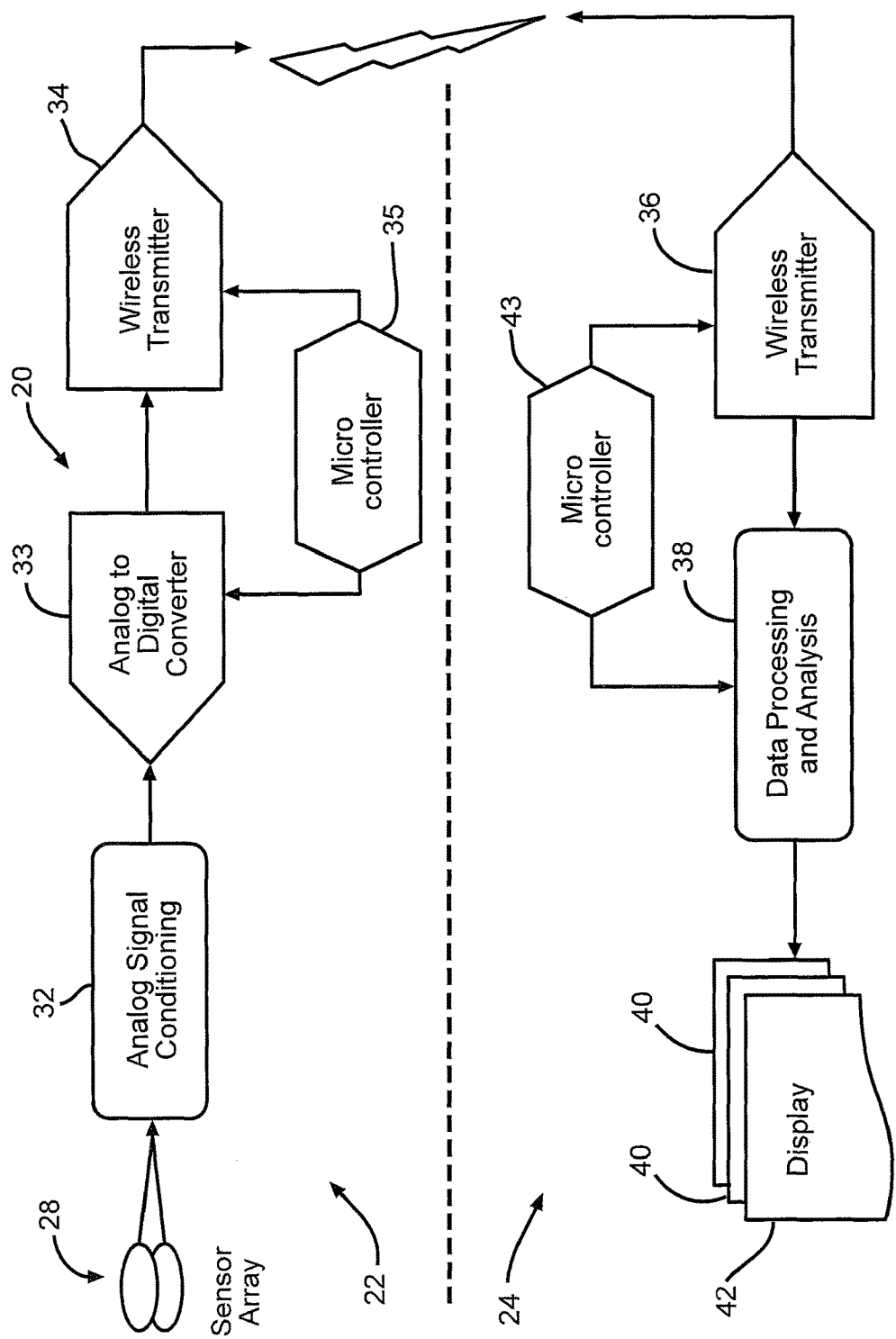
FIG. 2 is a block diagram and conceptual representation of a mTBI detection system incorporating wireless technology in accordance with the present invention.
Figure 2C:
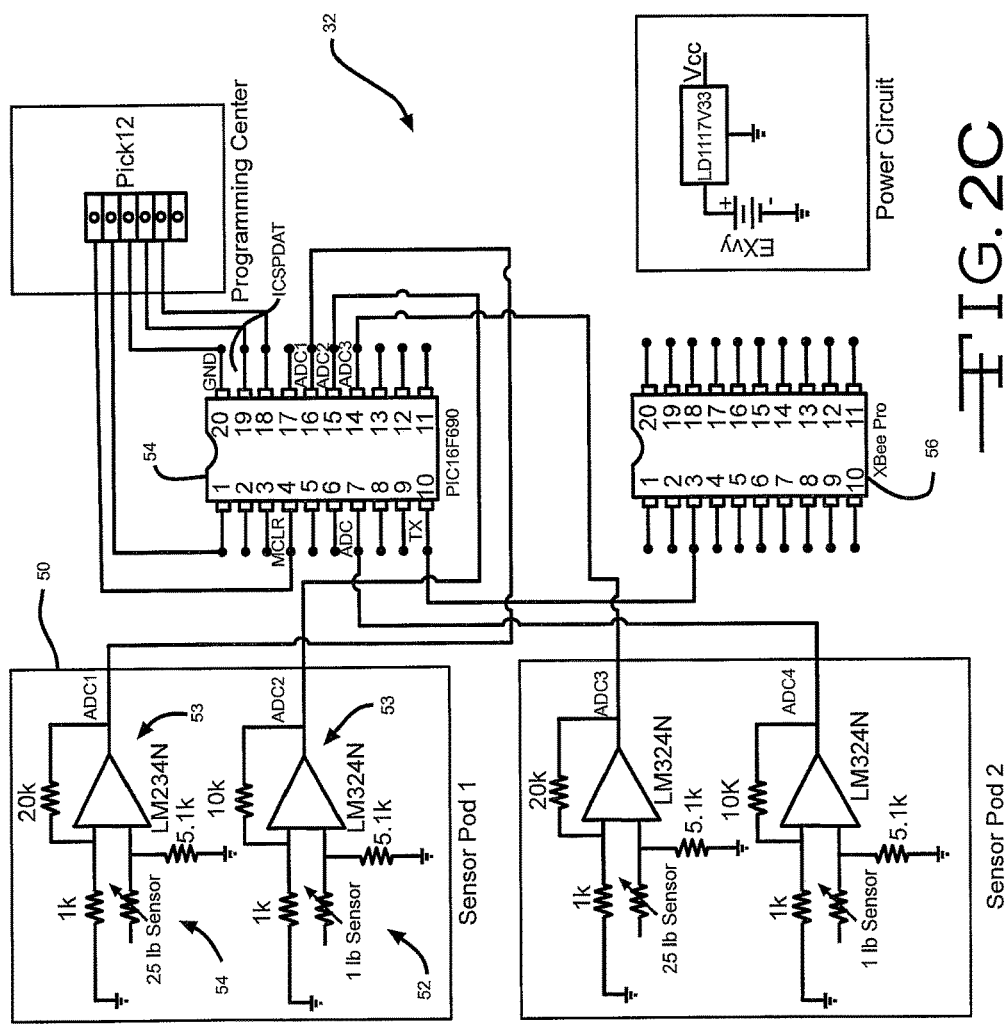
FIG. 2C is a schematic circuit diagram for a signal conditioning circuit that is included in the system shown in FIG. 2.
Figure 2D:
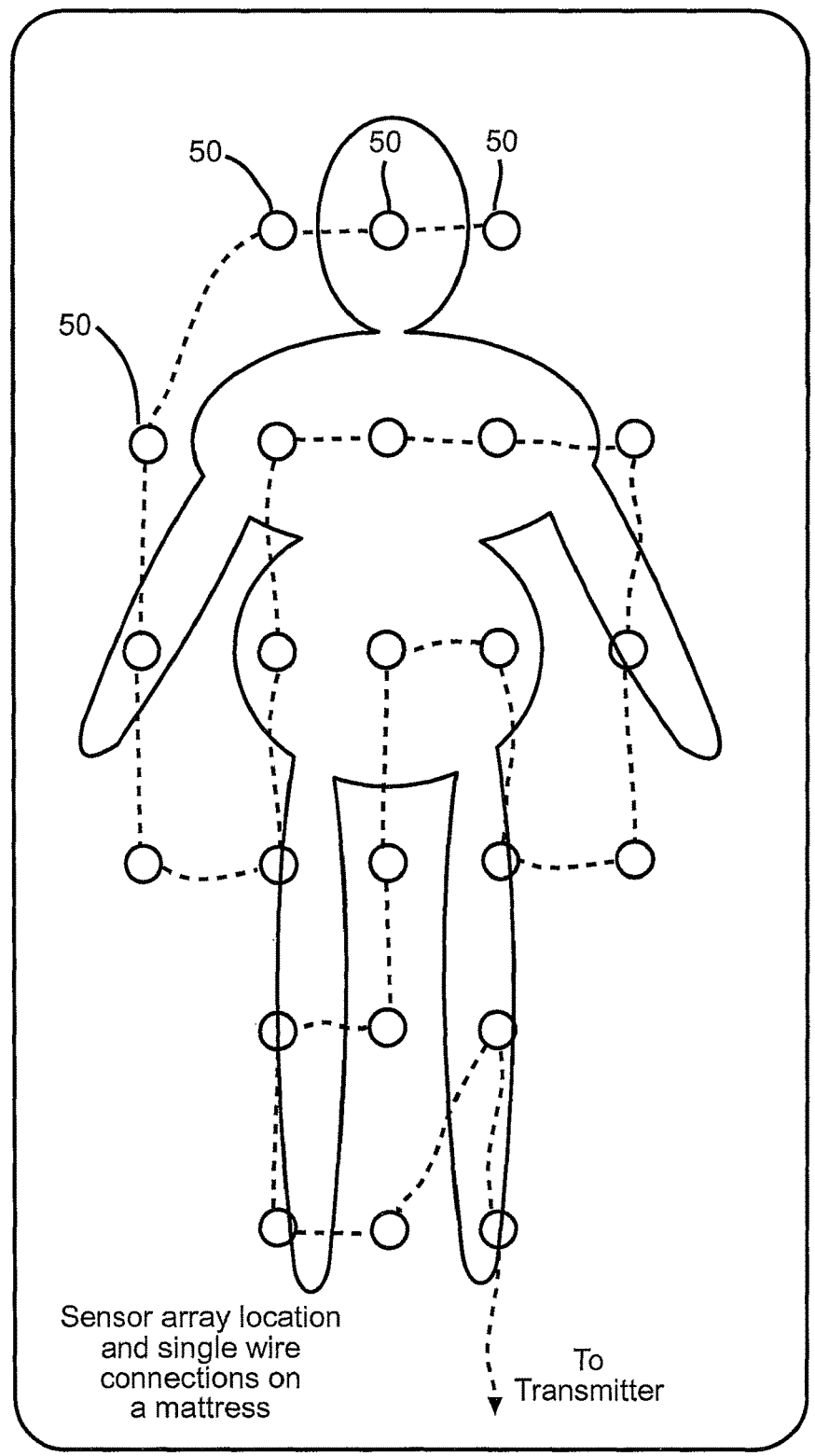
FIG. 2D illustrates a sensor array that may be utilized in the present invention.

According to a further embodiment of the system, the invention comprises an actigraphic device 20, as illustrated in FIG. 2, for detecting brain injury having a means for wireless transmission of signals and data. The device 20 is used to diagnose mTBI. The device includes a data collection portion 22, as shown above the dashed line in FIG. 2, and a data processing portion 24, as shown below the dashed line in FIG. 2. The data collection portion 22 includes a mattress 26 with a sensor array 28, a typical example of which is illustrated in FIG. 2D, a sensor battery (not shown), a signal conditioning unit 32, an analog to digital converter 33 and a wireless transmitter 34. The data collection portion 24 is controlled by a first computer processor, microcontroller or microprocessor, 35. The data processing portion 24 includes a wireless receiver 36, a data processing and analysis device 38 that includes software employing novel algorithms for data processing and analysis, a data storage device 40 and a display unit 42. The data collection portion 24 is controlled by a second computer processor, microcontroller or microprocessor, 43. While the device 20 has been described above as utilizing batteries and wireless transmission of data, it will be appreciated that the invention also may be practiced with other power supplies, such as, for example commercial alternating current electricity. Additionally, the portions 22 and 24 may be hard wired together (not shown), thus eliminating the need for a wireless transmitter 34 and receiver 36. Additionally, a an Applied Specific Integrated Circuit (ASIC) may be utilized in place of the personal computer 16 shown in FIG. 1 or the control devices described above for the system 20 shown in FIG. 2.

The sensor array 28 includes multiple sensors that measure SM, heart rate, and respiration and are situated in close communication with the sleeping surface of the mattress. The sensors may be any highly sensitive sensors that detect movement and/or accelerometers such as are available from Analog Devices (model # ADXL346). The inventors utilized an innovative sensor pod 50 that is available from Tekscan Inc. under that name Flexiforce Sensor. As illustrated in FIG. 2A and that sandwiches two sensors 52 and 54 with different sensitivities of 1-lb and 25 lb, respectively, to enable sensing various loads. The 1-lb sensor 52 provides a higher accuracy, but if it saturates, the 25-lb sensor 54 provides a higher dynamic range. A more detailed description of the Flexiforce Sensor is provided in U.S. Pat. No. 5,989,700. In the configuration shown in FIG. 2, the system 20 may be used to monitor various sized patients from infants to adults. Outputs of both sensors 52 and 54 contained in each sensor pod 50 are available at the microcontroller for intelligent seamless processing of data.

The sensors 50 are extremely thin (208 um) and flexible, allowing them to be easily manipulated and unobtrusive on the sleep surface. They are imbedded in a small, waterproof mattress pad (not shown). The sensing areas are ⅜ inch diameter polyester film with pressure-sensitive ink sandwiched between two conductive layers. The conductance between these two layers varies directly with the force applied orthogonally to them. The sensors are capable of operating with high linearity and low hysteresis and drift as depicted in Figure-2B.

The mattress pad with the sensors 50 is placed beneath standard sleep bedding making it non-obtrusive to the sleeping surface. Since the sensors 50 are exceptionally small and lightweight, they are not disruptive of patient sleep. The mattress pad containing the sensors 50 is portable and can be used noninvasively in a home, in a sleep laboratory or at a hospital bedside. To insure the capture of sleep movements during normal posture and sleep position changes during the night, the sensors 50 are arranged across the sleep surface, and linked to provide both integrated and spatially segregated movement estimation. An exemplary arrangement of a plurality of the sensors 50 is illustrated in FIG. 2D, where only a few of the sensors are provided with a numerical identifier. The sensors respond to a change in pressure in less than 5 microseconds, meaning that they can be accurately sampled at 200,000 samples per second; however, with regard to the present invention a variable sampling rate of around 10 samples per second is sufficient for the purpose of mTBi detection. Sensor output signals were tested by the inventors with two independent methods. Analog analysis of signals using oscilloscopes were performed in a laboratory. In addition, digital signals collected by a prototype system in a wireless fashion were examined to check the device performance. These two sets of independent tests verified the suitability of this novel movement detection architecture that enables product flexibility for use in patients of various weights and ages, from infants to adults. Outputs of both pairs of sensors are available at the microcontroller for intelligent seamless processing of data. In addition, sleep respiratory movements are captured and future device development is planned to examine the autonomic regulatory correlative between sleep movement phasic peaks and respiratory rate/quality.

As the sensor array 28 is affected by SM, with signals from the sensors are relayed by wire to the signal processing, or conditioning, unit 32 which is located in close proximity to the sensor array. Within the conditioning unit 32 the signal may be amplified, filtered, and/or isolated, etc., and is otherwise made ready for wireless transmission. A schematic circuit diagram for the signal conditioning unit 32 is shown in FIG. 2C. In the preferred embodiment, the signal conditioning unit 32 centers on a PIC16F690 microprocessor 54 that is capable of operating at 20 MHz; however, other similar microprocessors or ASCI's also may be utilized. The microprocessor 54 uses low power and provides a Universal Synchronous Asynchronous Receiver Transmitter (USART) module, I2C, ADC and additional GPIO ports. In the circuit shown in FIG. 2C, the microprocessor 54 is used to collect the sensor readings and supply the collected sensor data to an on-board Analog to Digital Convertor (ADC) 56. The ADC 56 converts the sensor data into a digital format in preparation for wireless transmission. The digital data is then supplied as a data stream to the wireless transmitter 34.

Before the microprocessor 54 can sample the piezoresistive sensors 50, their outputs need to be converted in a resistance-to-voltage amplifier. This circuitry needs to be modified for piezoelectric sensors. Accordingly, as shown in FIG. 2C, a non-inverting resistor-ladder amplifier 53 is included as an interface between each of the sensors 52 and 54 and the microprocessor 54. The gain for the amplifiers connected to the 25-lb sensors amplifier is greater than the gain for the amplifiers connected to the 1-lb sensor in order to improve the sensor sensitivity.

The wireless transmitter 34 that is used is capable of transmitting up to 18 dBm power, giving it an effective line-of-sight range of 1 mile, thus making it suitable for health care campuses. The power transmitter level can be decreased to save power at the cost of transmission distance for home based applications. The transmitter 34 receives a stream of digital bits, packages them into 4 bit messages and then selects one of the 16 even parity quasi-orthogonal pseudo-random codes presented in Table-1. Each 32 bit code is further partitioned into smaller 2-bit symbols to chose one of the 4 possible constellation points of a Offset Quadrature Phase Shift Keying (OQPSK) Modulation scheme. Each selected constellation point is then transmitted using a 2.4 GHz complex carrier. These measures are required for noise and interference mitigation as well as enabling multiuser and network operations. The transmitter 34 also provides the functionality of networking many sensors together to allow monitoring of multiple patients simultaneously. The wireless transmitter 34, which may be either integrated with the signal conditioning unit 32 or located in close proximity thereto, transmits the conditioned signal to the wireless receiver 36.

TABLE 1

| Message | Even Parity Quasi-orthogonal Code |
|---------|-----------------------------------|
| 0000    | 11011001110000110101001000101110  |
| 0001    | 11101101100111000011010100100010  |
| 0010    | 00101110110110011100001101010010  |
| 0011    | 00100010111011011001110000110101  |
| 0100    | 01010010001011101101100111000011  |
| 0101    | 00110101001000101110110110011100  |
| 0110    | 11000011010100100010111011011001  |
| 0111    | 10011100001101010010001011101101  |
| 1000    | 10001100100101100000011101111011  |
| 1001    | 10111000110010010110000001110111  |
| 1010    | 01110111000110010010101100000111  |
| 1011    | 01110111101110001100100101100000  |
| 1100    | 00000111011110111000110010010010  |
| 1101    | 01100000011101111011100011001001  |
| 1110    | 10010110000001110111101110001100  |
| 1111    | 11001001011000000111011110111000  |

The wireless receiver 36 may be in close proximity to the transmitter 34 but is preferably far enough from the transmitter to isolate the sleeping patient from persons involved with controlling the SM monitoring and data analysis activities of the system 20. In another alternate embodiment the transmitter is a transceiver (not shown) functioning to receive input relating to the control of sensor sampling and signal conditioning and is situated remotely from wireless receiver 36. The invention also contemplates replacing the wireless receiver 36 with a second transceiver (not shown) to allow transmission of control signals from the data processing portion 22 of the system 20 to the data collection portion 24 of the system.

On the receiver side of the wireless transmission, the transmitted SM signal data is demodulated using OQPSK method, decoded using parity check and spread spectrum techniques and processed in the receiving portion 24 of the system 20. The receiving portion 24 is integrated with or in close proximity to the wireless receiver 36. A processor 38 within the receiving portion 24 is configured to process and analyze data after it is received in accordance with software and related algorithms of the invention. Also within or in close proximity to the receiver 36 and processor 38 are a data storage device 40 and a display 42 that are in communication with the processor and are operable to control the system 20. The data storage device 40 and a display 42 also store and display processed and analyzed data.

During system operation signals from the sensors 50 are amplified to fluctuate between 0 and 5V. The processor 32 then converts the analog voltage into a digital value between 0 and 1023. This value directly correlates with how much pressure the sensor currently senses and is then sent serially to the transmitter 34. The receiver 36 transmits via USB to the host computer 48. A bridge was designed and implemented by the inventors to communicate between wireless modules and USB port. Additionally, the inventors enhanced both the USART communication between the microcontroller 35 and wireless module 34 as well as algorithms to receive data on the computer/receiver side.

Figure 3:
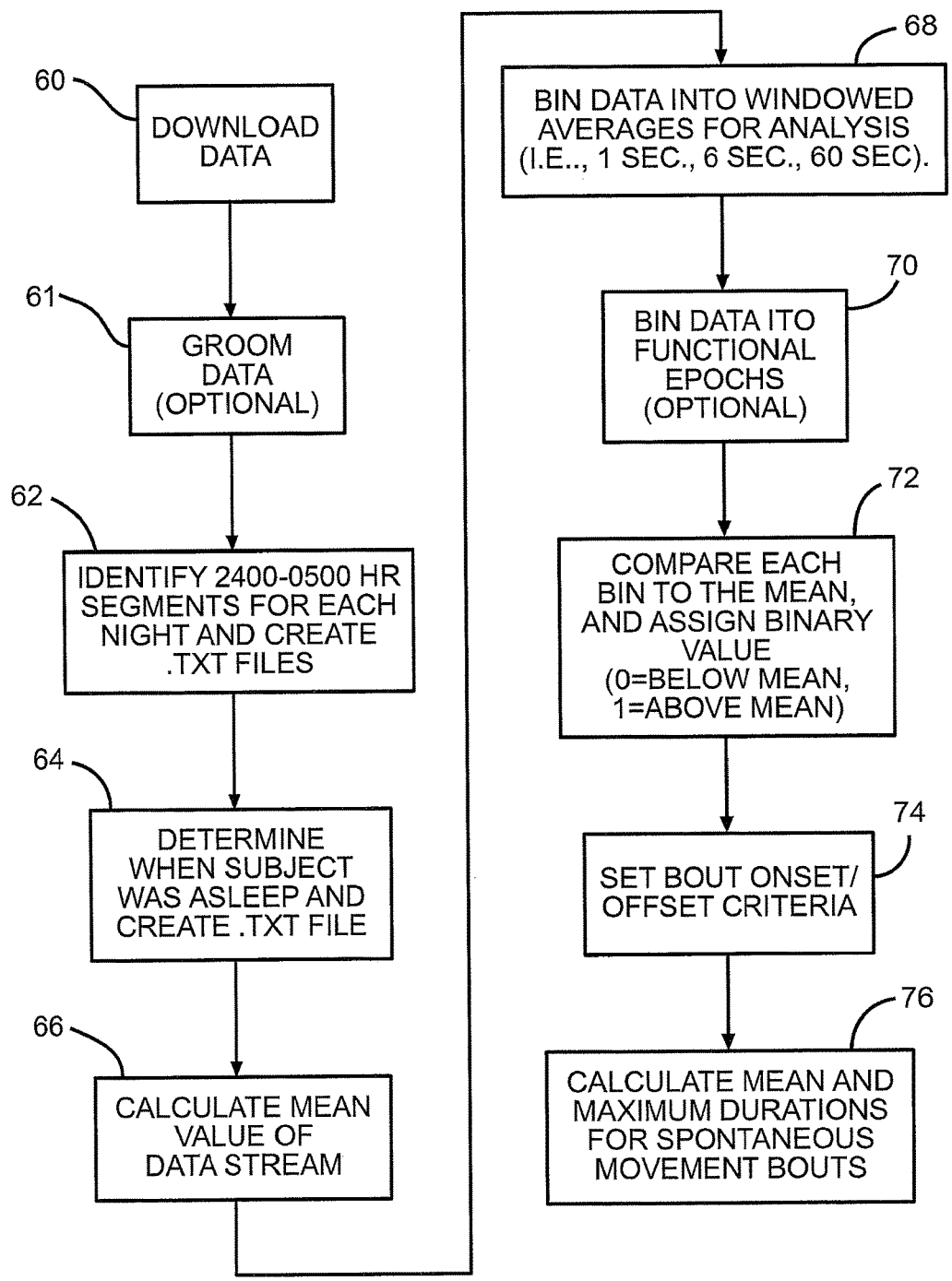
FIG. 3 is a flow chart description of a sleep-related movement data processing algorithm found in the present invention.

A flow chart description of a SM data processing algorithm is shown in FIG. 3. The algorithm shown computes data of SM bout temporal structure to reflect both micro- and macro-structural features of sleep movement and quiescence bouts. For SM analyses which strive to uncover primitive SM fast cycle activity, i.e., circa 1 cycle per minute, behavior arousals and frank wake epochs are removed from the data stream using data grooming methods. Behavioral arousals, awakenings, and wake epochs are changed to empty, or place holding time intervals, in the actigraphic data which effectively holds their time place for time frequency analyses.

What constitutes a "sleep period" can be defined based on video or a caregiver sleep diary with infants, or with adults, a patient sleep diary. FIG. 3 uses a midnight to 5:00 AM (2400-0500 hours) time period for illustration, but the whole or a part of a sleep period can be examined provided there is sufficient data. In addition to analysis of sleep periods, algorithms may be used to identify more idiosyncratic parameters of sleep such as sleep movement level or intensity. To analyze such parameters a central tendency measure, e.g., a mean, can be computed as a reference.

Referring again to FIG. 3, an absolute value of digitized output is derived from groomed SM data, and used to determine an average actigraphic digitized value. The flow chart is entered through functional block 60 in which denoised data from the actigraphy device, i.e., the sensors 50 contained in the mattress 26, is downloaded. The downloaded data is then groomed in functional block 61 as described above. This step is shown as being optional, since it is only needed if SM fast cycle activity is being evaluated. Next, time segments for each study period are identified in functional block 62 and supplemental data, such as the subject's sleep diary is utilized to determine the segments during which the subject was actually asleep in functional block 62. The data for the time segments during which the subject was not asleep are then discarded from further study.

Preferably, the magnitude range of movement across a sleep period is individualized so that known idiosyncratic individual differences in the magnitude of local movements and the quantitative relationship between relative levels of movement vs. quiescence is customized. Accordingly, a mean value of the data stream is determined in functional block 66 and the value is recorded to establish a referent average value representative of the range of movement velocity expressed during the sleep period selected. The algorithm then proceeds to functional block 68 where the time-frequency data at 15 Hz are binned into categories that reflect fast cycle spontaneous movements: 1 second, 6 seconds, 12 seconds, or longer epochs of 1 or 3 minutes to examine quiescence continuity or evidence of arousal intrusion or sleep fragmentation. Next, in functional block 70, the data are binned into epochs based on functional objectives, i.e. determination of sleep movements, or sleep fragmentation. However, this step is shown as being optional and may be omitted. As illustrated in FIG. 3, the objective is to determine SM frequency and duration.

SM detection typically requires short bin sizes, e.g. 1, 6 and 12 seconds for determining the microstructure of the SM bout number and size. In functional block 72, bin averages are determined and compared to a grand mean for assignment of 0 or 1 values depending on whether the average value for a bin is above or below the average session referent. Next, in functional block 74, a bout onset/offset criteria, which is the number of zeros allowed before a specific bout is terminated, is determined. Finally, in functional block 76, mean and maximum durations are calculated for spontaneous movement bouts consisting of sequences of ones and for quiescent bouts consisting of sequences of zeros. Thus, the method shown corrects for individual differences in size, weight, gender, age, etc., that influence sensor velocity, as well as individual differences in the amount of movement and is not corrected by existing commercial devices.

Figure 3A:
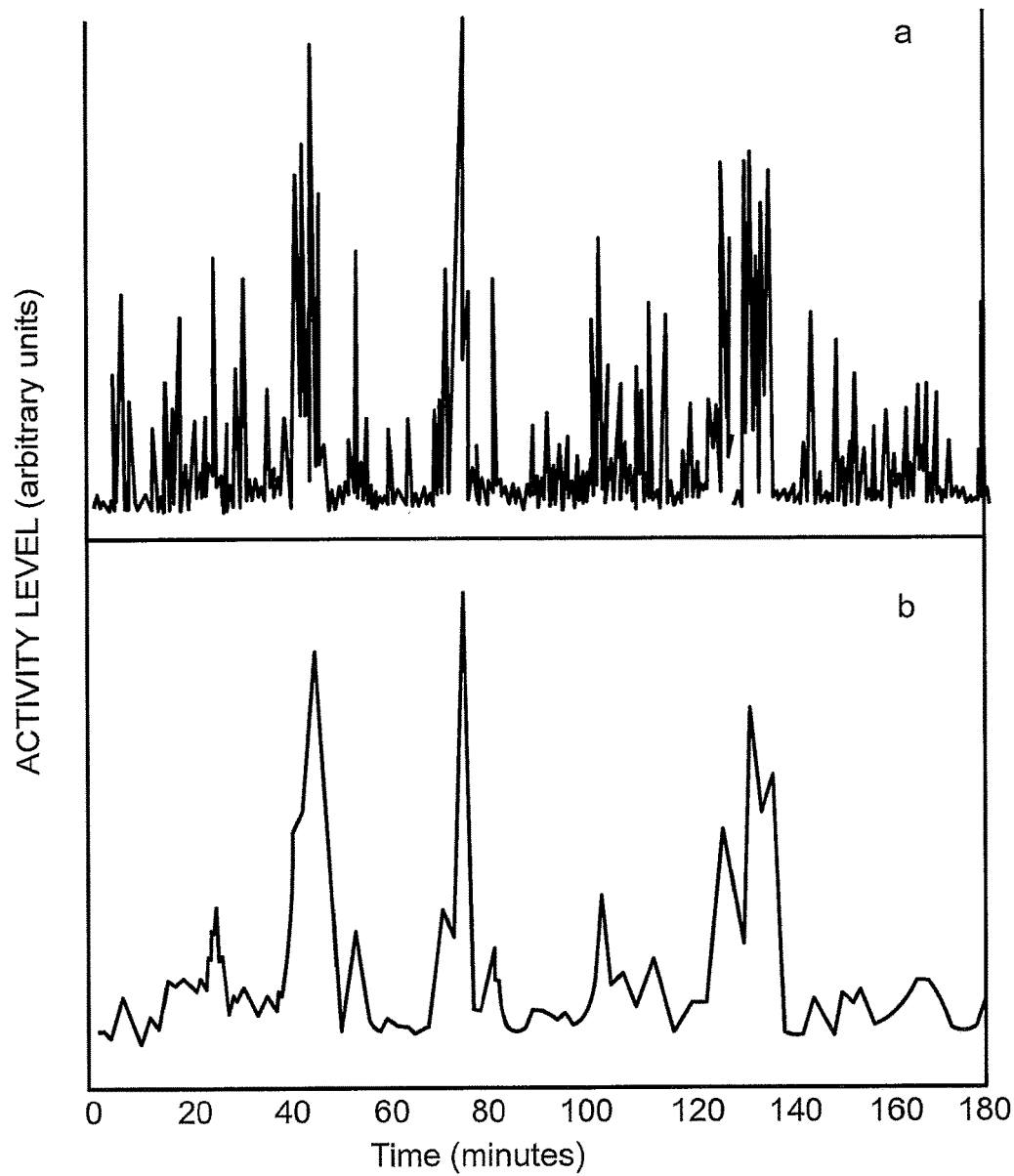
FIG. 3A shows data before and after processing with the algorithm illustrated in FIG. 3.

The present invention also contemplates varying the A/D sampling rate as appropriate for the sleep analysis feature of interest. For example, the upper graph in FIG. 3A illustrates a raw data signal is shown while the lower graph in FIG. 3A shows the same data following 10 s epoch bin conditioning. The analysis method integrates the SM values and assigns a binary code of 0/1 based on the patient's SM full or partial night average. The inventors have found SM estimate verity with as small as 2 hours of sleep data. The software algorithm utilized in the present invention corrects for individual differences, which vary greatly based on the age and basal activity level of the subject, and produces patient performance summaries of SM parameters and basic sleep-wake measures. The inventors have validated these measures with EEG and video-graphic measures as is standard in sleep science practice and plan to continue this confirmation with further testing in an ASMA Veterans Administration laboratory.

Referring now to data processing and analysis according to the invention, software is provided to program the computer processor 38 of the receiving portion 24 of the system 20. The software analyzes Bout structure to yield a measure of temporal distribution of movement bouts that quantifies the number, average duration, and maximum duration of SM. Quiescence bouts are analyzed in a mirror fashion with wider bins to detect sleep fragmentation following sleep onset. In addition to bout structure analysis, subjects may be monitored for cyclic properties related to SM rhythms, sleep state, and feeding rhythms. Quiescence bout decrements in state related analyses are an index of sleep fragmentation and are often confirmed in longer state related spectral analyses having 30 to 60 minute cycles. Parameters such as SM amplitude, timing, burst, arousability and sleep fragmentation may all be compared to identify abnormal sleep movement patterning and sleep cycle dysfunction using similar variant algorithms. Cyclic properties of SM in the 1 to 5 minute range, as well as other state and homeostatic rest activity patterns may be. analyzed using software.

Since the movements representative of altered SM parameters are often very slight, a high sensitivity and fidelity of the system is crucial for detecting SM characteristic of brain injury. Preferably the monitoring device is capable of detecting very minimal movements at relatively high sample rates that are greater than, or equal to, 10 Hz. FIG. 4 represents an example of SM measured using a typical prior art device during a consolidated sleep period. As illustrated, data collected is erratic and made largely ineffective by 'data deserts" of zero values registered even as SM occurs. The present invention improves significantly upon data collection from typical results obtained with prior art equipment, an example of which is shown in FIG. 4. Available actigraphic devices use software that is tuned to measure sleep-wake distinctions (e.g. sleep onset, sleep arousals, or awakenings, etc) rather than low amplitude, higher frequency SM. Available measurement devices are not sensitive to the range of low amplitude (force detection) and high frequency (sampling rate) movements in the SM system, and therefore, neither monitor nor analyze information on SM bout structure or distribution. Notably, available measurement devices are not sufficiently sensitive to low amplitude SM and therefore, it is not possible to either access or process SM data in the commercial software with adequate efficiency. Further, the sampling rate even in specialized versions of the available measurement devices is typically limited to 0.5 Hz while standard integrated sampling resolution limits with available devices are even worse, being on the order of 0.15 Hz. The present invention has high sensitivity with load variance between less than 1 g and up to 25 lbs SM and sampling rate parameters of up to 200 KHz to detect SM patterning. Additionally, the present invention has the flexibility to analyze conventional measures of sleep-wake to evaluate CNS injury and status.

Figure 5:
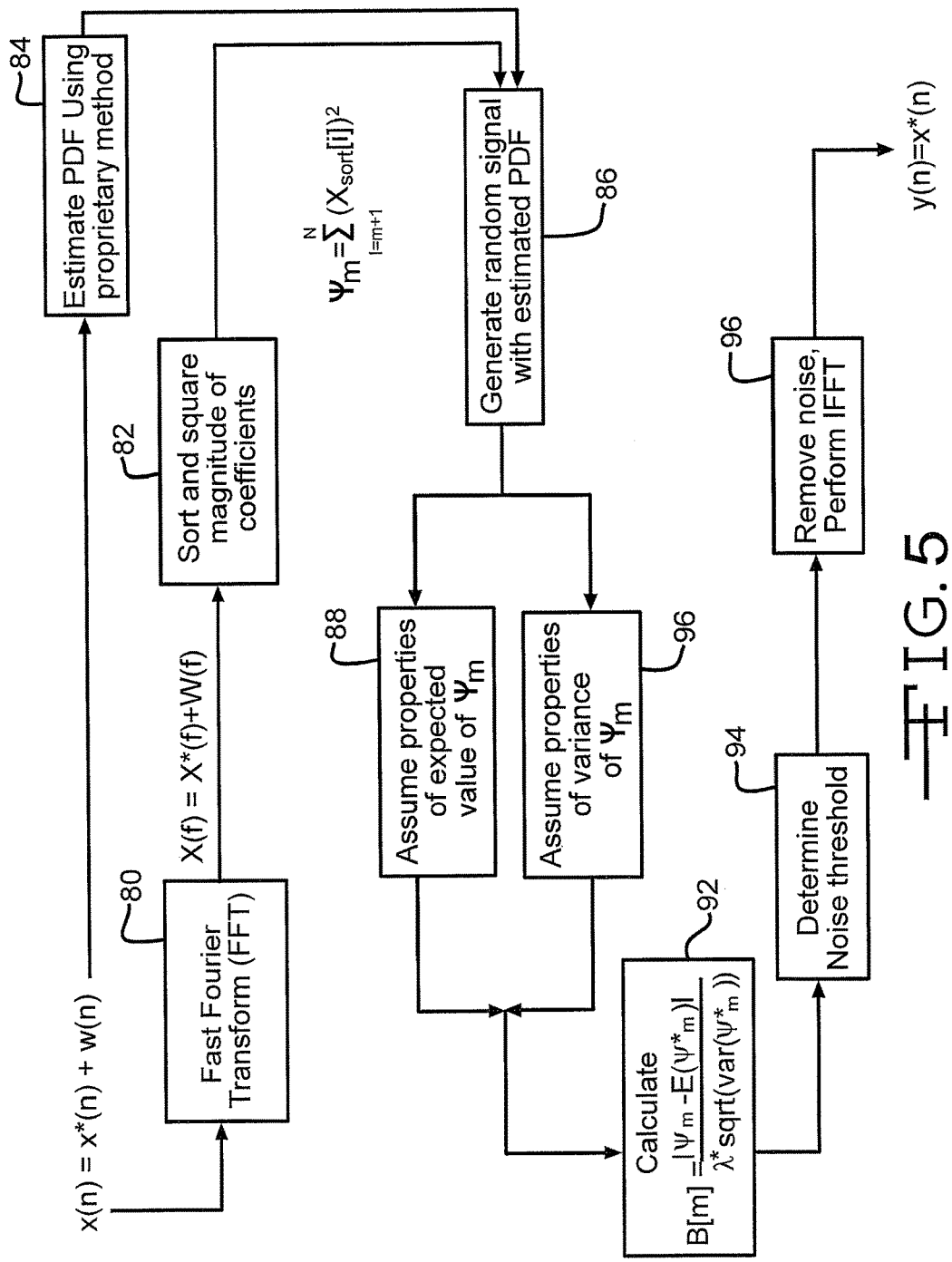
FIG. 5 is a block diagram of a de-noising algorithm functioning in the receiving station of the present invention.

In addition to incorporating appropriately sensitive sensors within the sensor array, the sensitivity of the brain injury detection system of the present invention may be enhanced with inclusion of smart circuits or algorithms for de-noising or other post conditioning functions for processing the sensor data. A block diagram of a de-noising algorithm for use with the present invention is illustrated in FIG. 5. In order to remove noise, the frequency spectrum is used to determine a soft threshold by first projecting the signal onto an orthogonal basis. Coefficients are then sorted in descending order, squared and summed to produce a soft threshold. Once the noiseless coefficients have been determined, noisy coefficients are removed in the frequency domain and the original signal is reconstructed in the time domain. Accordingly, in functional block 80 a Fast Fourier Transform (FFT) is applied to the input data x(n) which includes a data component x*(n) and a noise component w(n). The FFT Coefficients are then sorted and squared in functional block 82 to produce the function $\psi_m$, which is the energy sorted signal in the frequency domain. Concurrently with the operations shown in functional blocks 80 and 82, a Probability Density Function (PDF) is estimated using a novel method for the input data in functional block 84. In functional block 86, the function $\psi_m$ and the estimated PDF are utilized to generate a random signal. The properties of the expected value and the variance of the generated random signal are assumed in functional blocks 88 and 90, respectively. The assumptions assumed in functional blocks 88 and 90 are then used in functional block 92 to calculate B [m], a function related to the noise present in the signal. A noise threshold is determined in functional block 94 and then utilized in functional block 96 to remove the noise component. The remaining signal is then subjected to an Inverse FFT (IFFT) to reconstitute the input data without the noise y(n) which is equal to x*(N).

Sleep movement data are collected dynamically and parsed by sleep movement algorithms which have been developed by the inventors over years of research. The temporal distribution of arousal-independent, sleep movements are identified, and temporal sequences of conditioned data are examined for bout structure, intermediate arousal events and general sleep quality, such as, for example, sleep onset time, arousal number and duration, sleep fragmentation, etc., are also estimated. The output returns a string of parameters related to the organization of fast cycle movements that meet criteria for "sleep movement" bursts, such as "r" frequency, duration and maximum bout duration, range values, as well as the same distribution information for quiescent bout events. These parameters are used to characterize the typicality of patient sleep movement patterning, and to inform the health care provider regarding patient sleep quality or fragmentation, estimation of sleep deprivation, such as, for example, suppression of sleep movement bout features, decreased arousals, and other standard actigraphy sleep-wake information on sleep latency, arousals/awakening after sleep onset, time to sleep onset, total sleep, etc. Clinical trial data will provide EEG and video data to determine the relationship between device performance and the standard assessments. However, the unique focus of the present invention is a quantitative rendering of the temporal organization of sleep movements and the corollary of brain injury status.

The system 20 resolves the shortcomings of earlier actigraphic devices by being unintrusive to sleep movement patterning and adequately sensitive to generate signals representative of SM which is altered in brain injured patients. Abnormal brain function is correlated with precise temporal parameters of sleep-related spontaneous movements. These movements are related to fundamentals of sleep organization, are specifically distinguished from arousal events, and are impaired in patients with various determinants of brain injury. Thus, abnormal movement characteristics in patients with brain damage are identifiable when analyses of bout microstructure and rhythmicity of sleep-related movements are compared to the normal sleep architecture, i.e., bout microstructure and rhythmicity of sleep-related movements, of subjects without brain injury.

According to the present invention, methods of monitoring and analyzing actigraphy data are used to screen, detect, test, diagnose, or otherwise evaluate brain injury. In particular, the methods are most applicable to detecting brain injury such as mTBI which may impart only subtle cognitive dysfunction or other clinical indications and therefore is not adequately detectable by current existing methods.

In a preferred embodiment, the invention is used to screen patients for suspected brain injury such as mTBI that would be subsequently confirmed by additional testing. Patients may be suspected of having mTBI based on one or more clinical indications. In addition to modified sleep behavior, symptoms of mTBI or concussion include seizures, headache, nausea, vomiting, weakness, fatigue, impaired sight or smell, depression, irritability, dizziness and impaired cognitive function. Cognitive function may be assessed by employing a variety of tools including the Ranchos Los Amigos Scale or Glasgow Coma Scale during the acute period and standard neuropsychological assessments in the following weeks.

In a second preferred embodiment, the present invention is used to confirm the diagnosis of brain injury in a patient having one or more clinical indications as described herein or after conventional methods have proven to be inconclusive. In still another embodiment, patients are evaluated because they have experienced a blow to the head, an ischemic or hypoxic episode, neurotoxicity, or the like, that has placed them at high risk for being afflicted by brain injury.

Patients may be monitored at any time but are preferably monitored during the night so as to encourage representative sleep behavior. They should be made comfortable in a quiet surrounding with minimal distractions. The sensor array may be incorporated within the sleeping surface of the patient's mattress for minimal intrusion, separate from the mattress as in the case of optical sensors, or may be in contact with the patient directly. If data will be generated from sensors fitted to the patent's anatomy the sensors should be attached at locations which can be expected to change position during sleep such as the wrists or ankles. Duration of SM monitoring periods may be less than a full night so long as sufficient data is generated for analysis.

As the patient sleeps, a sampling rate is used which returns signals from the sensors appropriate to a particular parameter of interest. In general, signals pertaining to fine grained analysis of SM bout vigor, duration, amplitude and organization must be sampled at higher rates than signals pertaining to sleep acquiescence or fragmentation. Preferably, signals are sampled at a rate of between 0.3 and 10 Hz.

After a significant amount of signals are sampled, they are evaluated for particular sleep characteristics and abnormal sleep architecture. The analysis of sleep architecture can be performed at varied levels of sophistication but preferably the identification of sleep parameters is accomplished using algorithms derived from previous testing of patient populations similar to the patient being monitored. Preferably, the onset and offset of particular SM parameters are identified based on thresholds established for individual patients in light of the variation and intensity of signals collected for a particular monitoring duration.

Once SM parameters are identified from the sensor signals, the parameters are attributed a value and compared to the SM of populations unaffected by brain injury. Patients having statistically significant dampened sleep movements are assigned a determination of present brain injury. Comparisons between the patient sleep parameters are performed using statistical methods. Preferably, the determination of a threshold value for detection of clinically significant brain injury is performed by receiver operating characteristic plot analysis.

To reiterate, SM analyses require high device sensitivity and specificity for adequate data resolution to parameterize the features of the SM bout structure, periodicity, etc and to evaluate quiescence bout structure (inverse function) to analyze sleep fragmentation. The present invention utilizes an algorithm that is flexible in arranging the lens of structural analyses to incorporate microstructural organization for SM analysis, and conventional macrostructural sleep-wake analyses, and can be adjusted for the norms in different age, weight and other relevant demographics.

Data and Analysis

To investigate the relationship between brain injury, sleep disorder, and SM suppression, the inventors studied data derived from brain injured newborns and 2-4 month old infants at risk for brain injury. Infants at high risk for brain injury because of neurotoxic exposure to alcohol were studied with polysomnography, videography, and actigraphy using a 10×10 mm piezoelectric device. In subsequent studies, infants at high risk for brain injury because of severe apnea and bradycardia were compared to normative preterm infants. The apneic infants were being treated with high dose methylanthines, such as caffeine or theophylline, known to disrupt sleep. In additional studies, nighttime actigraphic measurements of normal and schizophrenic adults were compared. Based on the experimental findings and analysis from these and other studies, the inventors confirmed previous animal findings and characterized the nature of sleep related spontaneous movements in neonate to adult populations.

Figure 6:
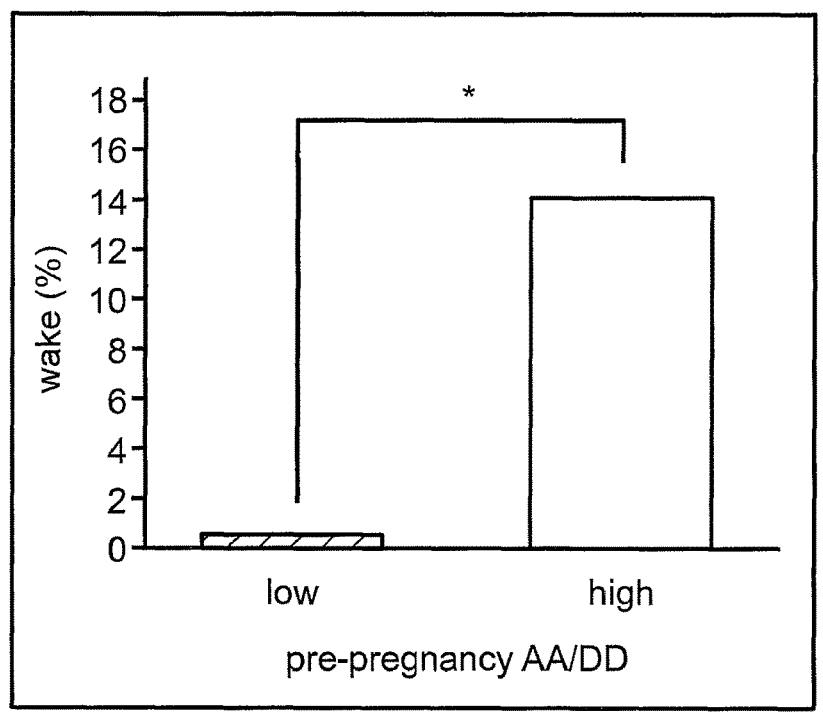
FIG. 6 illustrates abnormal sleep fragmentation in patients with neurotoxic exposure to alcohol.

Infants at high risk for brain injury exhibit sleep disorder, e.g. accumulated sleep deprivation, and sleep fragmentation, when compared to matched controls. Sleep disorder characterized by polysomnography and videosomnography shows increased sleep fragmentation, as determined by the number of arousals following sleep initiations, in patients with neurotoxic exposure to alcohol as illustrated in FIG. 6. Determination of behavioral states, according to conventional methods, revealed that the percent waking state after sleep onset was significantly greater in infants with more neurotoxic alcohol exposure.

Sleep deprivation associated with decreased alertness can be related to the level of prenatal alcohol exposure. Table 2 shows correlations between poor daytime alertness and unsettled behavior (e.g. irritability) in infants with increased alcohol exposure assessed by absolute alcohol (AA) per binge or per drinking day (DD).

TABLE 2

|  | Alertness | Unsettled/Irregular |
|---|---|---|
| AA/Binge | −0.570* | 0.502 |
|  | N = 21 | N = 21 |
| Retrospective |  | 0.468 |
| AA/DD |  | N = 21 |
| Five or more drinks | −0.762* |  |
| prior to knowledge | N = 20 |  |
| of pregnancy |  |  |

$p < 0.05$,
*$p < 0.01$, binge = >5 drinks per occasion

Figure 7:
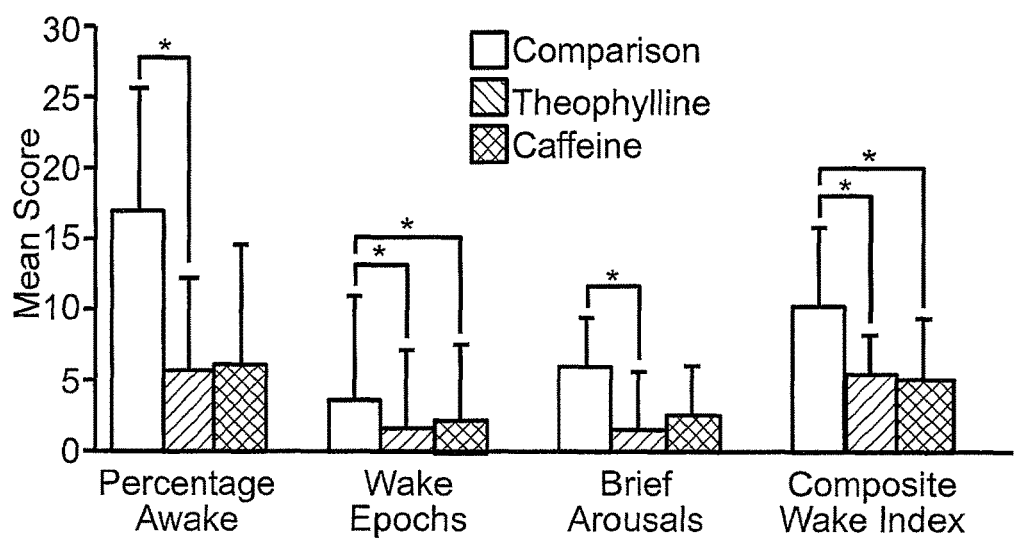
FIG. 7 illustrates decreased arousability during sleep of apneic infants at high risk for brain injury.

Similarly, in a study of premature infants suffering from apnea, sleep disorder was evident in videographic analysis of actigraphy, sleep, and waking episodes. However, when sleep deprivation (consequent to sleep disorder) was assessed, the infants showed reduced arousability during sleep. As shown in FIG. 7, high-risk premature infants with apnea showed sleep deprivation effects marked by fewer arousals. The arousal events of the brain injured infants (theophylline and caffeine groups), were significantly lower than controls, reflecting reduced arousability, possibly due to extended (average=12.4 days) high dose methylxanthine treatment.

Figure 8:
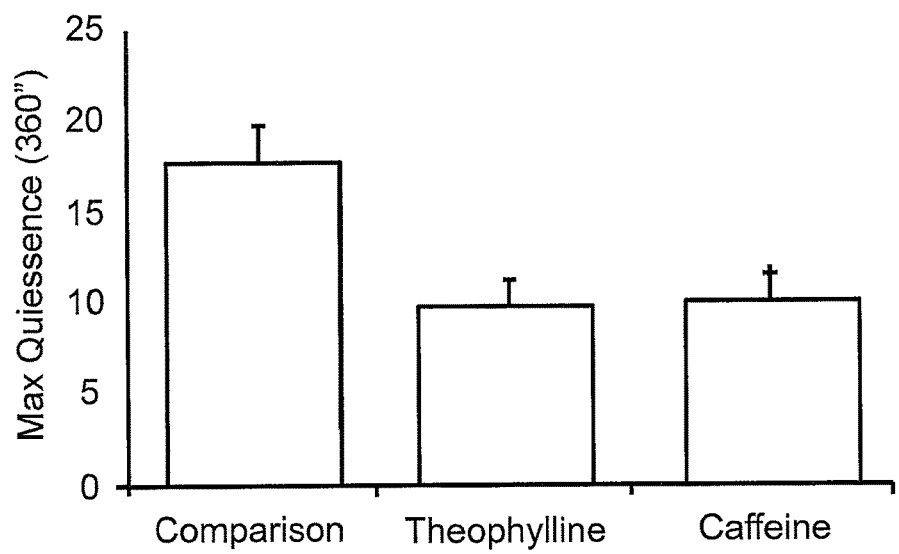
FIG. 8 illustrates increased sleep fragmentation during sleep of apneic infants at high risk for brain injury.

The seemingly inconsistent finding in sleep-wake patterns between the two infant groups reflected chronic sleep deprivation. Alcohol exposed infants showed sleep disorder and reduced daytime attention and irritability; while methylxanthine infants showed reduced arousability compared to controls. Algorithmic assessment of sleep disorder examines movement values that are below average for the individual actigraphic output and bins the raw data into larger bout sizes more reflective of state as a measure of sleep disorder or fragmentation. Applying a time related movement algorithm to detect sleep continuity and fragmentation revealed that average quiescence period macrostructure was consistently reduced in both groups of at-risk infants. The algorithm for sleep fragmentation uses large, state-like (6 nun) bins as a correlated marker of sustained sleep across the sleep period. As shown in FIG. 8, sleep fragmentation in apneic infants treated with xanthines is reflected in significantly lower duration of sustained quiescence associated with uninterrupted sleep periods, as compared to healthy preterm controls.

Figure 9:
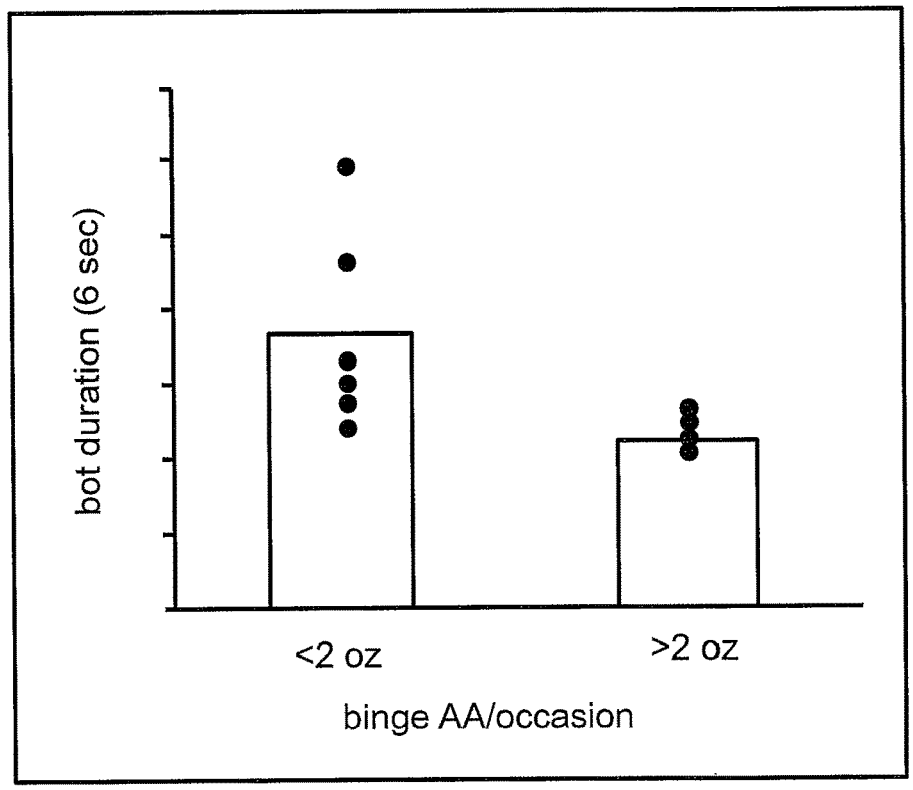
FIG. 9 illustrates reduced sleep movement bout duration of infants exposed to alcohol.
Figure 10:
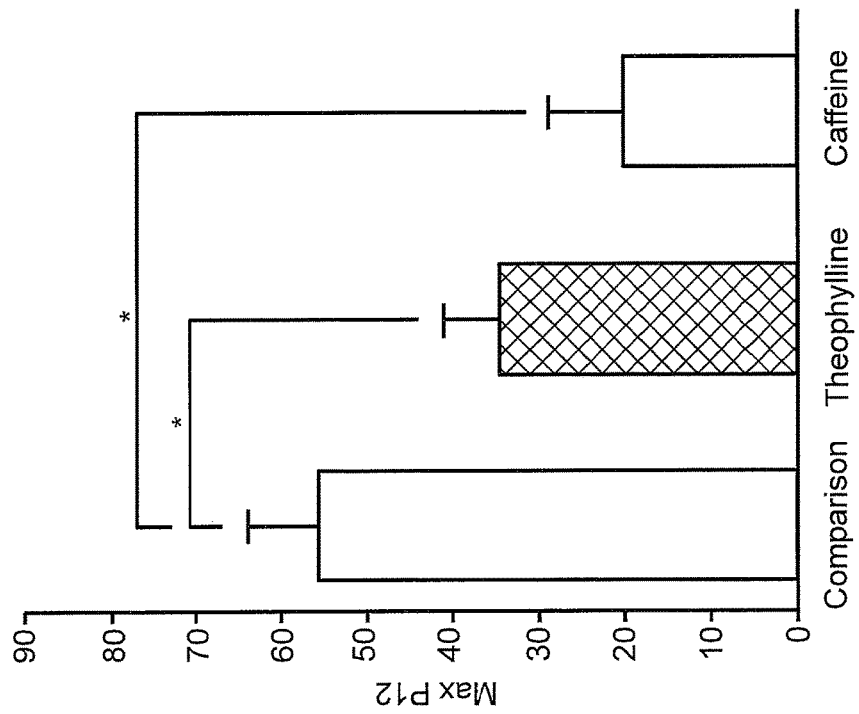
FIG. 10 illustrates reduced sleep movement bout duration of apneic infants.

In addition to sleep fragmentation reflected in reduced quiescence, both groups of infants at risk for brain injury show reduced SM bout duration during sleep. The robustness of SM patterning was measured with an algorithm for bout structure pattern analysis. High alcohol-exposed infants show significantly reduced SM duration, and infants exposed to more than 2 oz of alcohol per occasion showed greater SM bout duration deficits than infants exposed to lower levels, as illustrated in FIG. 9. Similarly, preterm apneic infants showed reduced SM bout durations when compared to a control. FIG. 10.

Figure 11:
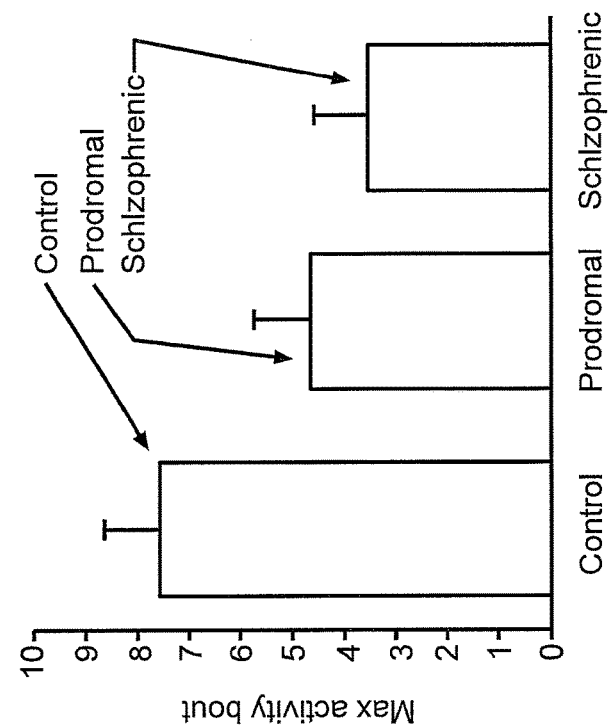
FIG. 11 illustrates dampened SM activity of adult and adolescent schizophrenic populations in proportion to their severity of brain injury.

The inventors compared sleep patterns of adult and prodroinal adolescent ($1^{St}$ episode) schizophrenics to normative features of sleep architecture using methods of analysis that they developed during the prior infant studies. Actigraphy was collected using a commercially available prior art device and analyzed using standard software in parallel with multi-parameter algorithms according to the present invention. Examination of the data stream with the analysis methods of the invention revealed group differences not available in the prior art software packages. Both groups of schizophrenics showed diminished sleep movement activity compared to controls. SM bout structure algorithms of the invention best revealed group differences in SM activity. As illustrated in FIG. 11, SM activity suppression was exhibited according to the severity of brain injury. As expected, SM amplitude was greatest in the control populations that were understood to be without brain injury. The adolescent group, understood to have only intermediate brain injury, showed only moderate suppression of SM while the adult group, having suffered the longest from chronic schizophrenia demonstrated the most severe suppression of SM activity.

Figure 12:
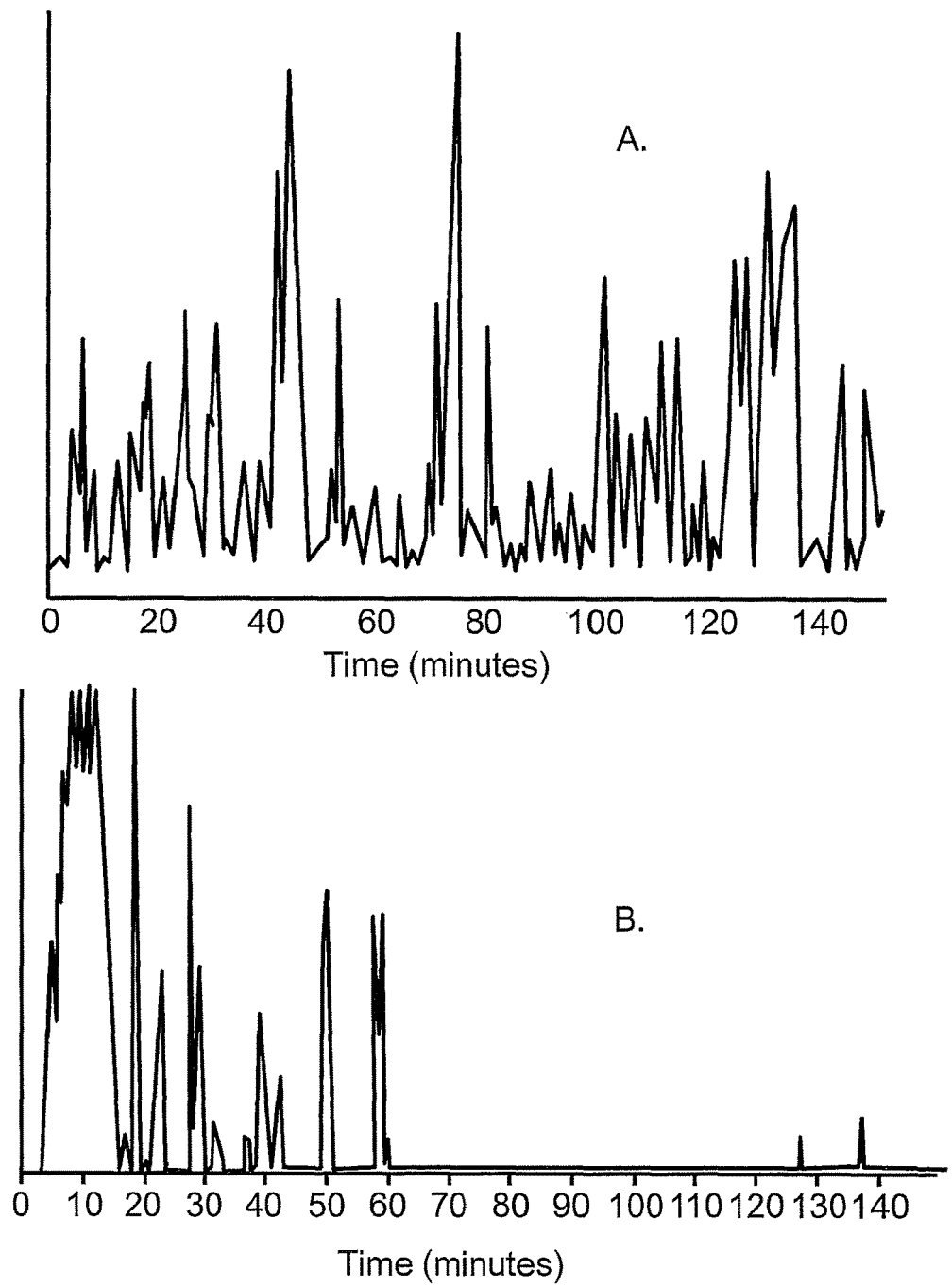
FIG. 12 compares data obtained with the system shown in FIG. 2 with data obtained from a prior art actigraphic device.

The inventors also have compared prototypes of the present invention to commercially available prior art actigraph devices. The data collected with the present invention is shown in FIG. 12A while the data collected with the prior art device is shown in FIG. 12B for a three hour sleep period. A comparison of the data reveals a lower sensitivity to SM signals during the 2nd half of the recording in data from the prior art device. With the prior art device, SM is essentially absent for 50% of the three hour sleep period. This "data desert" appears to be typical of sleep recordings with commercially available prior art actigraphy devices that are tuned to detect large movement events such as awakenings, but not high frequency, low amplitude SM events. Hence, a comparable sleep period test using the prior art device captures only a small portion of the available sleep movement across the night period. As described above, the present invention utilizes a thin mattress pad with embedded sensors and normal bedding above it. Thus, it is unobtrusive to sleep and not detected by the sleeper. In contrast, the prior art device uses a watch attached by a strap and metal clasp to the wrist for an adult, or ankle for an infant, which can cause skin irritation after several days.

Figure 13:
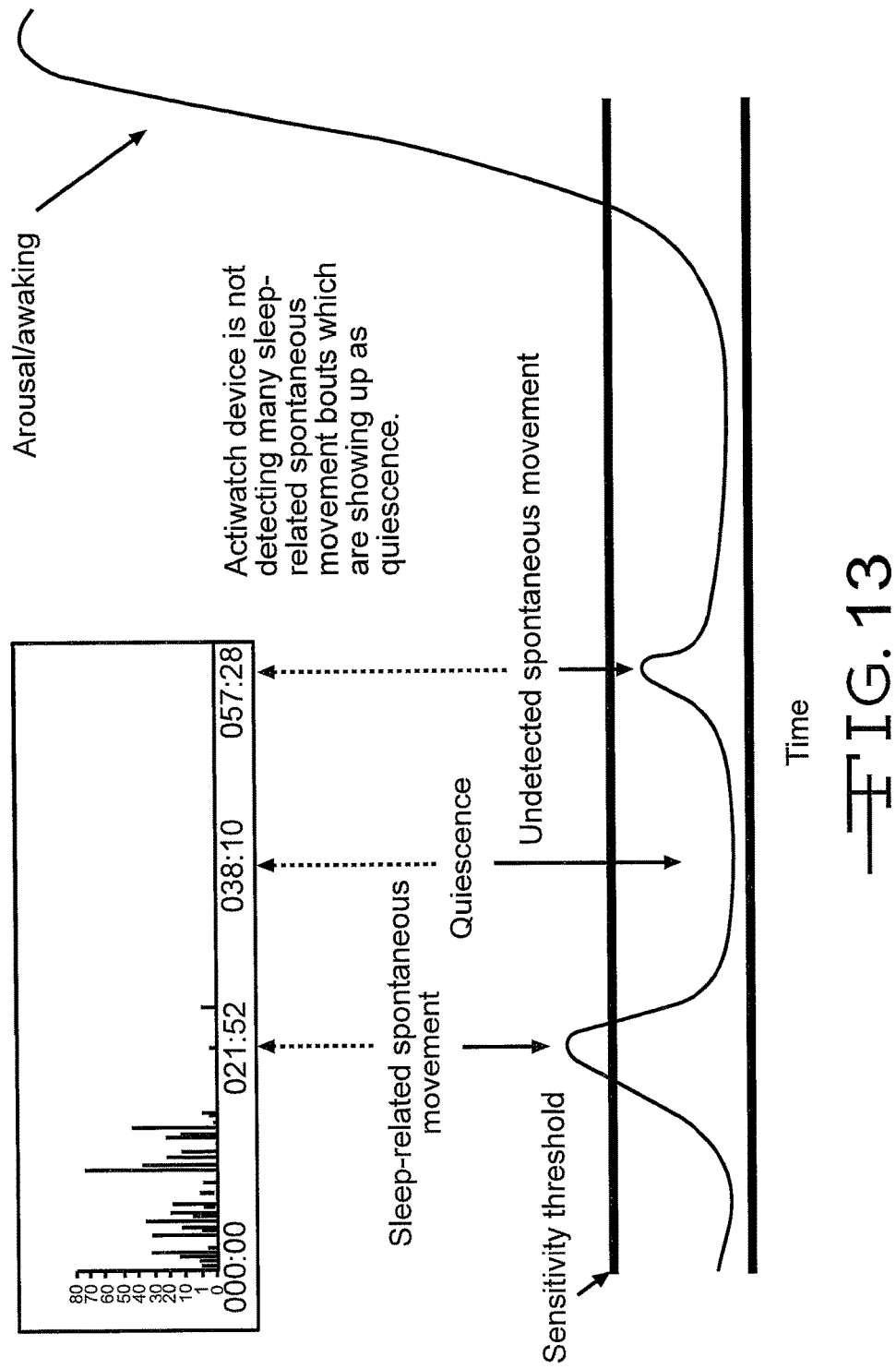
FIG. 13 illustrates a fundamental design difference between system shown in FIG. 2 and a typical prior art actigraphic device.

FIG. 13 illustrates a fundamental design difference between commercially available prior art watch devices and the method of the present invention and emphasizes the difference in the macrostructural prior art device vs. the microstructural approach of the present invention. The tracings in FIG. 13 are data from the conventional prior art actigraph device output which is acceptable for detecting sleep-wake state, arousals/awakenings, etc. and matches reasonably well to video but not EEG analyses. Notably, the prior art device is not sufficiently sensitive to low amplitude SM and therefore, neither accesses nor processes SM data in the prior art software with adequate efficiency. Further, the sampling rate even in specialized versions of the prior art watch method is limited to 0.5 Hz while standard prior art integrated sampling resolution limits of 0.15 Hz are even worse. Trade secrets for the triaxial accelerometer used in watches do not specify threshold for movement counts, however, form analysis of test data, the inventors believe that their data show that they are too high to detect SM in a sleeping patient. In contrast, the present invention has high sensitivity (load variance is as low as <1 g up to 25 lbs) and specificity for SM sampling rate parameters (up to 200 KHz) to detect SM patterning as well as the flexibility to analyze conventional measures of sleep-wake to evaluate CNS injury and status.

Furthermore, available prior art actigraphic devices use software that is tuned to measure sleep-wake distinctions (e.g. sleep onset, sleep arousals, or awakenings, etc) rather than low amplitude, higher frequency SM. Available prior art measurement devices are not sensitive to the range of low amplitude (force detection) and high frequency (sampling rate) movements in the SM system, and therefore, neither monitor nor analyze information on SM bout structure or distribution.

The prototype of the present invention exhibits both a broad range of movement detection, including valuable respiratory movements which are coupled with the SM pattern generator. The timing, vigor and duration of SM are known to upregulate respiration and cardiac function and display irregular, but reliable, periodicity that is in the window of asphyxiation (1-5 minute). SM improves airway motor tone and increase cardiorespiratory rate and sympathetic tone functioning as a primitive arousal system during sleep. The inventor's research has shown that SM bout duration is suppressed in brain injury patients, periodicity is disrupted, and sleep deprivation effects are evident.

The Present invention is designed to improve upon prior device devices by being uniquely sensitive and specific to SM and respiratory movements during sleep, a characteristic not present in current prior art actigraphy devices. Because the present invention is based on cutting-edge technology, it functions efficiently when imbedded in a sleep surface. This feature is a significant advance over sleep diagnostic devices that are intrusive to ongoing sleep. The wireless sensor is portable, potentially reusable, and suitable for sleep studies in a hospital (scalable or home environment. SM distribution and bout features can be exhaustively tabulated and analyzed by the software algorithms to identify SM parameters as well as more conventional measures of sleep disorders to evaluate patient brain injury status.

Laboratory sleep testing has show that the present invention has high sensitivity and specificity to capture low amplitude sleep movements and SM bout structure reliably, with the increased capacity of the integrated sensor system, can integrate respiratory changes related to SM bouts (i.e. respiratory volume and frequency increases following sleep which are an additional measurement parameter for sleep integrity/loss estimates), and associated autonomic regulatory function.

CONCLUSION

Incidence statistics suggests that the military need for early diagnosis of mTBI reflects a national crisis. An estimated 1.4 million TBI-affected civilians are identified each year. TBI contributes to 30% of accidental deaths and 75% of these injuries are concussions or other forms of mTBI. More than $60 billion of healthcare costs were identified in 2000. The present invention is designed to offer a new and unobtrusive method for early detection of mTBI that can be utilized in the home or field as well as the bedside. The inventors estimate, based on their prior research, that both traumatic and nontraumatic sources of neurological impairment will reflect abnormalities with this method.

It should now be readily apparent to those skilled in the art that a novel system and methods for detecting brain injury has been provided. The present invention is not to be limited in scope by the aspects and embodiments disclosed herein, which are intended only as exemplary illustrations of the invention. Various changes, modification, and equivalents in addition to those shown or described herein will become apparent to those skilled in the art and are similarly intended to fall within the spirit and scope of the invention whether or not they exist in the following or amended claims. For example, while the actigraphic sensors have been illustrated as described as having sensitivity ranges of zero to one pound and zero to 25 pounds, the invention also may be practiced utilizing actigraphic sensors having other measurement ranges and using different technologies.

What is claimed is:

1. A device for detecting brain injury by measuring sleep movement parameters comprising:
   a plurality of sensors, each operative at a sampling rate of at least 10 Hz to generate a plurality of temporally-associated data signals relating to sleep movements of a subject, said sensors arranged to provide both integrated and spatially segregated movement estimation for said subject, at least some of said sensors having a sensitivity capable of detecting load variances as small as 1 g;
   a signal conditioning module including a conditioning circuit in communication with said plurality of sensors, said signal conditioning module operative to condition said data signals;
   a processor in communication with said signal conditioning module, said processor operative to analyze said conditioned data, said processor having a module programmed for parsing the data into a plurality of bins of defined temporal duration, at least some of which bins are 60 seconds or less in duration, and for comparing the average values of each bin to differentiate among (a) bouts of quiescence, (b) bouts of macro-structural movements indicative of sleep or wake cycles, or sleep fragmentation; and (c) bouts of micro-structural movements, the micro-structural movements being useful to detect brain injury; and
   a non-inverting resistor-ladder amplifier as an interface between each of the plurality of sensors and the processor.

2. The device according to claim 1 wherein said plurality of sensors are arranged in a two dimensional array across a sleep surface, said array of sensors being in communication with said signal conditioning module.

3. The device according to claim 2 wherein said sensors are grouped in pairs of sensors at each location and further wherein each sensor pair includes two sensors having different sensitivity ranges to improve dynamic range.

4. The device according to claim 3 further including an analog to digital converter that is operative to convert analog signals obtained from said sensor array into a digital data stream for analysis by said processor.

5. The device according to claim 4 further including a wireless transmitter in communication with said analog to digital converter and a wireless receiver in communication with said processor, said wireless transmitter operative to transfer said digital data stream to said wireless transmitter for analysis by said processor.

6. The device according to claim 5 wherein said wireless receiver utilizes a method of Offset Quadrature Phase Shift Keying (OQPSK) Modulation.

7. The device according to claim 2 further including auxiliary sensors that measure at least one of heart rate and respiration, said auxiliary sensors being situated in close communication with said sleeping surface, and in communication with said signal conditioning module.

8. The device according to claim 1 wherein said processor is operative to identify within said microstructural movements a dampened pattern of sleep movement vigor characterized by at least one diminished parameter selected from a group consisting of movement frequency, vigor, bout organization, bout duration, amplitude, burst, and actigraphy-based measures of sleep fragmentation when compared to a value derived from sleep movement characteristics of a population without brain injury.

9. The device according to claim 8 wherein said processor is further operative to assign a conclusion of brain injury to a subject demonstrating said dampened pattern of sleep movement.

10. The device according to claim 1 further including a module programmed for a de-noising operation that utilizes a Fast Fourier Transformation, an Inverse Fast Fourier Transformation, and Probability Density estimation to remove noise from the sensor signals.

11. The device according to claim 1 wherein said processor has a module programmed for:
(i) parsing the data into sets of bins of defined temporal duration, at least some bin sets being 60 seconds or less in duration, and other bin sets being more than 60 seconds in duration;
(ii) analyzing the data from bins that are more than 60 seconds in duration for bouts of quiescence and bouts of macro-structural movements indicative of sleep or wake cycles; and
(iii) analyzing the data from bins that are 60 seconds or less for bouts of micro-structural movements indicative of brain injury.

12. The device according to claim 1, wherein at least one of the sensors comprises a piezoelectric based passive pressure sensor in a metal-carbon sheet covered with a vinyl.

13. A method of testing a subject for brain injury comprising the steps of:
(a) monitoring the sleep movements of a subject using movement sensors operable at a sampling rate of at least 10 Hz to generate a plurality of temporally-associated data signals relating to sleep movements, wherein an output of the movement sensors is converted in a resistance-to-voltage amplifier;
(b) parsing the data at least once into a plurality of bins of defined temporal duration of 60 seconds or less, and determining an average value for each bin to differentiate bouts of micro-structural movements from bouts of quiescence and bouts of macro-structural movements;
(c) comparing the values for bouts of micro-structural movements to a threshold value that is indicative of brain injury; and
(d) assigning a determination of brain injury according to the outcome of the comparison.

14. The method of claim 13, further comprising:
parsing the data an additional time into sets of bins of defined temporal duration of more than 60 seconds in duration; and
analyzing the data from bins that are more than 60 seconds in duration for bouts of quiescence and bouts of macro-structural movements indicative of sleep or wake cycles.

15. The method of claim 14 wherein the data from a period identified as sleep fragmentation is used in a determination of brain injury.

16. The method of claim 14, further comprising discarding the sleep movement data binned in bins of duration of more than 60 seconds when the data indicates bouts of quiescence or bouts of macro-structural movements.

17. The method according to claim 13 wherein step (a) also includes monitoring at least one of heart rate and respiration for the subject and further wherein step (b) also includes modifying the determined value as a function of at least one of heart rate and respiration.

18. The method according to claim 13 further comprising identifying a period of 1-3 hours during which the data signals include no movements indicative of frank awakenings, and wherein step (b) includes the following sub-steps applied to the data of said period:
(b1) calculate a grand mean value for the data generated in step (a);
(b2) compare each bin to the grand mean and assign a corresponding binary value to each bin;
(b3) set movement bout onset/offset criteria; and
(b4) calculate mean and maximum durations for spontaneous microstructural movement bouts.

19. The method according to claim 18 wherein sub-step (b2) includes assigning a zero binary value when the bin is less than the grand mean and a unity binary value when the bin is greater than the grand mean.

20. The method of claim 13 wherein the determination of brain injury is made based on an analysis of bout frequency, bout duration, and interbout interval of microstructural sleep movements.

21. The method according to claim 13 wherein the bins of defined temporal duration of 60 seconds or less include bins of 1 to 12 seconds to obtain estimates for fast-cycle microstructural movements.

22. The method according to claim 13, wherein the movement sensors are capable of being sampled at 200,000 samples per second.

* * * * *